(12) United States Patent
Myers

(10) Patent No.: US 12,094,316 B2
(45) Date of Patent: Sep. 17, 2024

(54) FLIGHT CREW FATIGUE AND CONTROLLED REST MANAGEMENT SYSTEM

(71) Applicant: Seeing Machines Limited, Australian Capital Territory (AU)

(72) Inventor: Rama Myers, Australian Capital Territory (AU)

(73) Assignee: SEEING MACHINES LIMITED, Australian Capital Territory (AU)

( * ) Notice: Subject to any disclaimer, the term of this patent is extended or adjusted under 35 U.S.C. 154(b) by 0 days.

(21) Appl. No.: 17/572,480

(22) Filed: Jan. 10, 2022

(65) Prior Publication Data

US 2022/0230522 A1  Jul. 21, 2022

(30) Foreign Application Priority Data

Jan. 18, 2021  (AU) ................ 2021900093
May 14, 2021  (AU) ................ 2021901443
Jul. 13, 2021  (AU) ................ 2021902139

(51) Int. Cl.
*G08B 21/06* (2006.01)
*A61B 5/00* (2006.01)
(Continued)

(52) U.S. Cl.
CPC ............ *G08B 21/06* (2013.01); *A61B 5/1128* (2013.01); *A61B 5/18* (2013.01); *A61B 5/4809* (2013.01);
(Continued)

(58) Field of Classification Search
CPC ...... G08B 21/06; G06V 20/59; G06V 40/174; G06V 40/172; G06V 40/161;
(Continued)

(56) References Cited

U.S. PATENT DOCUMENTS

| | | | |
|---|---|---|---|
| 6,927,694 B1 * | 8/2005 | Smith | B60K 28/066 340/576 |
| 7,969,327 B2 | 6/2011 | Christophe et al. | |

(Continued)

FOREIGN PATENT DOCUMENTS

| | | |
|---|---|---|
| WO | 2018/170538 A1 | 9/2018 |
| WO | 2020/061650 A1 | 4/2020 |

OTHER PUBLICATIONS

Seeshubha, M., "Potentials of Physiological Signals to Implement a Wearable Drowsiness Detection and Warning System for Pilots" (2019), Theses and Dissertations, University of North Dakota.

*Primary Examiner* — Benyam Haile
(74) *Attorney, Agent, or Firm* — FisherBroyles, LLP; Jason P. Mueller

(57) ABSTRACT

Described herein is a pilot monitoring system (100) including a camera (106) configured to capture a plurality of digital images of an aircraft (104) cockpit including one or both of a pilot (102) and a co-pilot (103) and a processor (114) configured to process the captured images. The images are processed to determine an alertness state of the pilot (102) and/or the co-pilot (103) during operation of the aircraft (104) based on detected facial features of the pilot (102) and/or co-pilot (103) in the images. Processor (114) receives information indicative of a current phase of flight of the aircraft and displays a visualisation of the alertness level and/or determines a suitability of a controlled rest period for the pilot (102) or co-pilot (103) based on the alertness state of the pilot and (102)/or the co-pilot (103) and the current phase of flight. An alert is issued alert to the pilot (102) and/or co-pilot (103) including a determination of a suitability of a controlled rest period for either the pilot (102) or co-pilot (103).

28 Claims, 16 Drawing Sheets

(51) Int. Cl.
    *A61B 5/11*           (2006.01)
    *A61B 5/18*           (2006.01)
    *G06V 20/59*         (2022.01)
    *G06V 40/16*         (2022.01)

(52) U.S. Cl.
    CPC ............ *G06V 20/59* (2022.01); *G06V 40/161* (2022.01); *G06V 40/172* (2022.01); *G06V 40/174* (2022.01); *A61B 5/6888* (2013.01); *A61B 2503/22* (2013.01)

(58) Field of Classification Search
    CPC ....... A61B 5/1128; A61B 5/18; A61B 5/4809; A61B 5/6888; A61B 2503/22
    See application file for complete search history.

(56) References Cited

U.S. PATENT DOCUMENTS

| | | |
|---|---|---|
| 8,204,636 B2 | 6/2012 | Christophe et al. |
| 10,376,198 B1 | 8/2019 | Flaherty-Woods et al. |
| 2006/0245620 A1* | 11/2006 | Roques .............. B64D 45/0056 |
| | | 382/115 |
| 2011/0071873 A1 | 3/2011 | Vaughan et al. |
| 2012/0316845 A1* | 12/2012 | Grey .................... G06F 9/5094 |
| | | 703/2 |
| 2015/0339527 A1 | 11/2015 | Plummer et al. |
| 2016/0071393 A1* | 3/2016 | Kaplan .................. A61B 5/162 |
| | | 340/539.12 |
| 2016/0090097 A1 | 3/2016 | Grube et al. |
| 2018/0186234 A1 | 7/2018 | Mestha |
| 2019/0213429 A1 | 7/2019 | Sicconi et al. |
| 2020/0183382 A1* | 6/2020 | Schwindt ............... B64D 45/00 |
| 2020/0290740 A1* | 9/2020 | Rangan ................. G08G 5/003 |

* cited by examiner

FLIGHT CREW FATIGUE AND CONTROLLED REST MANAGEMENT SYSTEM

CROSS-REFERENCE TO RELATED APPLICATIONS

This application claims priority to Australian Patent Application No. 2021900093, filed Jan. 18, 2021, Australian Patent Application No. 2021901443, filed May 14, 2021, and Australian Patent Application No. 2021902139, filed Jul. 13, 2021, the entire contents of which is incorporated herein by reference.

FIELD OF THE INVENTION

The present application relates to subject monitoring systems and in particular to a system and method for monitoring an attention and/or cognitive state of a pilot and/or co-pilot of an aircraft.

Embodiments of the present invention are particularly adapted for performing fatigue risk management of a pilot and/or co-pilot of an aircraft and determining a suitability of a controlled rest period for either a pilot or co-pilot of an aircraft based on an alertness state of the pilot and/or co-pilot. However, it will be appreciated that the invention is applicable in broader contexts and other applications.

BACKGROUND

Like many transportation modes, the global aviation industry operates around the clock. However, unlike other transportation modes, global aviation operations pose unique challenges to humans in that aircraft traverse the globe at a pace that can disrupt flight crew's circadian rhythm, and as a result—impact a pilot's ability to obtain the sleep they require to perform their duties safely, and productively.

Any combination of long-haul flight, flying during the pilot's "Window of Circadian Low" (WOCL), duties with multiple take-offs and landings, and limited sleep quality and quantity (typically less than 5 hours in any 24 hour period), all can contribute to elevated levels of flight crew fatigue. Accident analysis suggests that flight crew fatigue can lead to elevated levels of risk during the approach and landing phases of flight, which are critical phases of flight that often demand an increase in flight crew workload and decision making.

The traditional regulatory approach to managing crewmember fatigue has been to prescribe limits on maximum daily, monthly, and yearly flight and duty hours, and require minimum breaks within and between duty periods. This approach comes from a long history of limits on working hours dating back to the industrial revolution. The approach reflects an early understanding that long unbroken periods of work could produce fatigue (now known as 'time-on-task' fatigue), and that sufficient time is needed to recover from work demands and to attend to non-work aspects of life.

In the second half of the 20th century, scientific evidence began accumulating that implicated other causes of fatigue in addition to time-on-task, particularly in 24/7 operations. The most significant new understanding concerns:

The vital importance of adequate sleep (not just rest) for restoring and maintaining all aspects of waking function; and Daily rhythms in the ability to perform mental and physical work, and in sleep propensity (the ability to fall asleep and stay asleep), that are driven by the daily cycle of the circadian biological clock in the brain.

This new knowledge is particularly relevant in the aviation industry, which is unique in combining 24/7 operations with trans-meridian flight.

In parallel, understanding of human error and its role in accident causation has increased. Typically, accidents and incidents result from interactions between organizational processes (i.e. workplace conditions that lead crewmembers to commit active failures), and latent conditions that can penetrate current defenses and have adverse effects on safety.

Prescriptive flight and duty time limits represent a somewhat simplistic view of safety—being inside the limits is safe while being outside the limits is unsafe—and they represent a single defensive strategy. While they are adequate for some types of operations, they are a one-size-fits-all approach that does not take into account operational differences or differences among crewmembers.

Controlled rest is a mitigation strategy to be used as needed in response to unanticipated fatigue experienced during flight operations. Controlled rest is the process whereby pilots may take a nap, while temporarily relieved of operational duties in accordance with carefully prescribed 'controlled rest' procedures, typically when part of an augmented—but sometimes two-man—operating crew during live flight. Controlled rest is an effective mitigation strategy to be used as needed in response to fatigue experienced during flight operations.

However, controlled rest events have associated risks, including:

The second pilot becoming drowsy, impaired, or falling asleep at the same time.

The controlled rest event being taken during a critical phase of flight, or too close to a critical phase of flight.

The controlled rest event causing the pilot or co-pilot to be in a drowsy state—possibly due to sleep inertia—during a subsequent critical phase of flight.

The controlled rest event allowing a pilot or co-pilot to enter a deep sleep state that results in increased drowsiness when wakened.

The controlled rest event allowing a pilot or co-pilot to nap for longer than the maximum approved duration.

Thus, the inventors have identified a need to better monitor and determine suitable controlled rest events for pilots and co-pilots of aircraft.

Any discussion of the background art throughout the specification should in no way be considered as an admission that such art is widely known or forms part of common general knowledge in the field.

SUMMARY OF THE INVENTION

In accordance with a first aspect of the present invention, there is provided a pilot fatigue monitoring method, including:

receiving, from one or more cameras, a plurality of digital images of an aircraft cockpit including one or both of a pilot and a co-pilot;

controlling an image processor to process the received images to determine an alertness state of the pilot and/or the co-pilot during operation of the aircraft based on detected facial and/or body features of the pilot and/or co-pilot in the images;

receiving flight information indicative of phases of flight of the aircraft; and rendering a visualisation of the alertness state of the pilot and/or co-pilot on a graphical user interface to display an alertness state for a current phase of flight and/or a recent phase of flight.

In some embodiments, the method includes the step of issuing one or more pilot briefings to the pilot and/or co-pilot during flight via an electronic flight computer based on the determined alertness state and flight information, wherein the briefing includes a current or future predicted fatigue level of the pilot and/or co-pilot.

In some embodiments, the method includes the step of receiving input indicative of sleep history and/or a recent duty history of the pilot and/or co-pilot and wherein the step of issuing one or more real time briefings to the pilot and/or co-pilot is based in part on the sleep/duty history input.

In some embodiments, the graphical user interface is part of an electronic flight bag.

In some embodiments, the method includes the step of determining a minimum alertness threshold for the pilot and/or co-pilot.

In some embodiments, the method includes the step of continuously monitoring the alertness state of the pilot and/or co-pilot.

In some embodiments, the one or more pilot briefings include a proposed rest schedule for the pilot and/or co-pilot.

In some embodiments, the method includes the step of determining a fatigue score of the pilot and/or co-pilot based at least in part on the determined alertness state.

In some embodiments, the method includes the step of transmitting one or both of the fatigue score or alertness state to a database accessed by ground crew for determining a future flight or rest schedule of the pilot and/or co-pilot.

In accordance with a second aspect of the present invention, there is provided a pilot fatigue monitoring system, including:
one or more cameras for capturing a plurality of digital images of an aircraft cockpit including one or both of a pilot and a co-pilot;
a processor configured to:
process the received images to determine an alertness state of the pilot and/or the co-pilot during operation of the aircraft based on detected facial and/or body features of the pilot and/or co-pilot in the images;
receive flight information indicative of phases of flight of the aircraft; and
a graphical user interface for displaying a visualisation of the alertness state of the pilot and/or co-pilot for a current phase of flight and/or a recent phase of flight.

In some embodiments, the processor is further configured to generate one or more pilot briefings, based on the determined alertness state and flight information, wherein the briefing includes a current or future predicted alertness level of the pilot and/or co-pilot.

In some embodiments, the graphical user interface is configured to display the one or more pilot briefings to the pilot and/or co-pilot during flight.

In some embodiments, the system includes a communications module for communicating one or more of the alertness level or one or more pilot briefings to a ground crew.

In accordance with a third aspect of the present invention, there is provided a pilot monitoring method, including:
receiving, from one or more cameras, a plurality of digital images of an aircraft cockpit including one or both of a pilot and a co-pilot;
configuring an image processor to process the received images to determine an alertness state of the pilot and/or the co-pilot during operation of the aircraft based on detected facial and/or body features of the pilot and/or co-pilot in the images;
receiving information indicative of a current or future phase of flight of the aircraft;
determining, based on the alertness state of the pilot and/or the co-pilot and the current phase of flight, an amount and/or type of a controlled rest period for the pilot or co-pilot; and
issuing an alert to the pilot and/or co-pilot including a determination of a controlled rest period for either the pilot or co-pilot.

In some embodiments, where appropriate permission is obtained, the processor is further configured to receive input indicative of sleep history and/or a recent duty history of the pilot and/or co-pilot and wherein the determination of a controlled rest period for the pilot or co-pilot is based on the sleep history.

In some embodiments, the method includes the step of detecting a controlled rest event for the pilot or co-pilot based on detection of a sleep state and a current phase of flight.

In some embodiments, the method includes the step of receiving input from the pilot or co-pilot to specify a controlled rest event.

In some embodiments, the method includes the steps of:
monitoring the alertness state of the pilot or co-pilot who is awake during a detected controlled rest period of either the pilot or co-pilot; and
issuing an alert if the pilot or co-pilot who is awake enters a distracted, low vigilance drowsy, asleep or incapacitated attention state.

In some embodiments, the alert includes an alert that a pilot is drowsy and which is issued to an in-aircraft crew rest facility within the aircraft to alert other flight crew members. In some embodiments, the alert includes a notification that a controlled rest period has been entered and which is issued to a cabin crew notification device to alert a cabin crew member. In some embodiments, the alert is issued to a ground terminal to alert a dispatch, safety or operations member of a controlled rest period.

In some embodiments, the method includes the step of detecting a sleep state of the pilot or co-pilot who is sleeping during a period of controlled rest.

In some embodiments, the method includes the step of monitoring a length of sleep of the pilot or co-pilot during a controlled rest period.

In some embodiments, the method includes the step of detecting a deep sleep state of the pilot or co-pilot and issuing an alert to the pilot or co-pilot if a deep sleep state is entered.

In some embodiments, the method includes the step of performing facial recognition on at least a subset of the digital images to detect an identity of the pilot and/or co-pilot.

In some embodiments, the method includes the step of performing object detection on at least a subset of the digital images to determine the presence of other people in the cockpit of the aircraft.

In some embodiments, the method includes the step of performing facial recognition on at least a subset of the digital images upon detection of a person in the cockpit who is not the pilot or co-pilot.

In some embodiments, the method includes the step of performing facial recognition on at least a subset of the digital images to detect a presence of known cabin crew members in the cockpit.

In some embodiments, the method includes the step of registering the timing of known cabin crew members in the cockpit during a period of controlled rest of the pilot or co-pilot.

In some embodiments, where permission is obtained and regulations allow it, the method includes receiving biometric information of the pilot and/or co-pilot from a biometric reader device. Preferably, the determination of a controlled rest period for either the pilot or co-pilot is based on the received biometric information. In some embodiments, the biometric information includes a heart rate signal from a heart rate monitor. In one embodiment, the heart rate monitor includes an Electrocardiography (ECG) device. In some embodiments, the biometric information includes a signal indicative of brain activity received from an electroencephalography (EEG) device.

In some embodiments, the detected facial features include eye features to determine an eye closure of the pilot or co-pilot. In some embodiments, the detected facial features include nose and/or mouth features to determine a head pose of the pilot or co-pilot. In some embodiments, the detected facial features include a pupil and/or iris of an eye to determine eye gaze direction of the pilot or co-pilot.

In some embodiments, the alertness state is calculated based at least in part on a detected body position of the pilot and/or co-pilot in the received images. By way of example, the detected body position may include a body shape, body posture (e.g. slumping or standing), torso position, head tilt, body size, arm position and leg position. In some embodiments, the alertness state is calculated based at least in part on detected head and/or body posture or motion of the pilot and/or co-pilot across a plurality of the received images. By way of example, body motion may be characterised at least in part by change in body posture, shape or position across a plurality of captured images. In some embodiments, the alertness state is calculated based at least in part on detected mouth movement of the pilot and/or co-pilot across a plurality of the received images. In some embodiments, the alertness state is calculated based at least in part on detected speech of the pilot and/or co-pilot.

In some embodiments, the information indicative of a current phase of flight of the aircraft is received from a flight management system of the aircraft.

In some embodiments, the alertness state is characterized at least in part by a drowsiness measure based on the Karolinska Sleepiness Scale or Samn-Perelli scale.

In accordance with a fourth aspect of the present invention, there is provided a pilot monitoring system, including:
one or more cameras configured to capture a plurality of digital images of an aircraft cockpit including one or both of a pilot and a co-pilot; and
a processor configured to process the captured images to:
determine an alertness state of the pilot and/or the co-pilot during operation of the aircraft based on detected facial and/or body features of the pilot and/or co-pilot in the images;
receive information indicative of a current phase of flight of the aircraft;
determine, based on the alertness state of the pilot and/or the co-pilot and the current phase of flight, an amount and/or type of a controlled rest period for the pilot or co-pilot; and
issue an alert to the pilot and/or co-pilot including a determination of a controlled rest period for either the pilot or co-pilot.

In some embodiments, the system includes a single wide angle camera positioned to simultaneously image the pilot and co-pilot. In other embodiments, the system includes two cameras with each camera positioned to respectively image one of a pilot or co-pilot.

In some embodiments, the system includes a weight sensor located in a seat of the pilot or co-pilot to sense a presence of the pilot or co-pilot in their seat.

In some embodiments, the system includes a heart rate monitor for monitoring a heart rate of the pilot and/or co-pilot.

In accordance with a fifth aspect of the present invention, there is provided a method of visually monitoring a non-resting pilot of an aircraft during a controlled rest period of a resting pilot, the method including:
detecting a controlled rest event for the resting pilot;
upon detection of a controlled rest event, receiving images of the non-resting pilot using a camera;
processing the received images to determine an alertness state of the non-resting pilot; and
issuing an alert to the pilot and/or co-pilot, a cabin crew and/or a ground crew if the non-resting pilot enters a predetermined alertness state.

In some embodiments, the step of detecting a controlled rest event for the resting pilot includes receiving images of the resting pilot and processing the received images of the resting pilot to detect of a sleep state of the resting pilot.

In some embodiments, the method includes the step of receiving images of the resting pilot during a controlled rest period and processing the received images of the resting co-pilot to determine an alertness state of the resting pilot.

In some embodiments, the method includes the step of issuing a wake up alert to the resting pilot once a period of controlled rest ends.

In some embodiments, the predetermined alertness states include a distracted state, low vigilance drowsy state, asleep state or incapacitated attention state.

In some embodiments, the alert is issued via a flight crew alerting system from the instrument panel of the aircraft. In some embodiments, the alert is issued via a cabin crew alert system.

In some embodiments, the resting pilot performs a controlled rest outside a cockpit of the aircraft.

In accordance with a sixth aspect of the present invention, there is provided a computer system or device configured to receive the determined alertness state and/or determination of a controlled rest period from the system according to the fourth aspect.

BRIEF DESCRIPTION OF THE FIGURES

Example embodiments of the disclosure will now be described, by way of example only, with reference to the accompanying drawings in which.

DESCRIPTION OF THE INVENTION

Embodiments of the system described below will be described with reference to imaging and monitoring an aircraft pilot. However, it will be appreciated that the system may equivalently image and monitor a co-pilot or aircraft crew member located in an aircraft cockpit.

System Overview

Referring initially to FIGS. 1 to 4, there is illustrated a pilot monitoring system 100 for capturing images of a pilot 102 and/or a co-pilot 103 during operation of an aircraft 104. System 100 is further adapted for performing various image processing algorithms on the captured images such as facial detection, facial feature detection, facial recognition, facial feature recognition, facial tracking or facial feature tracking, such as tracking a person's eyes, head pose tracking and body pose tracking. Example image processing routines are described in U.S. Pat. No. 7,043,056 to Edwards et al. entitled "Facial Image Processing System" and assigned to Seeing Machines Pty Ltd (hereafter "Edwards et al."), the contents of which are incorporated herein by way of cross-reference.

Figure 1:
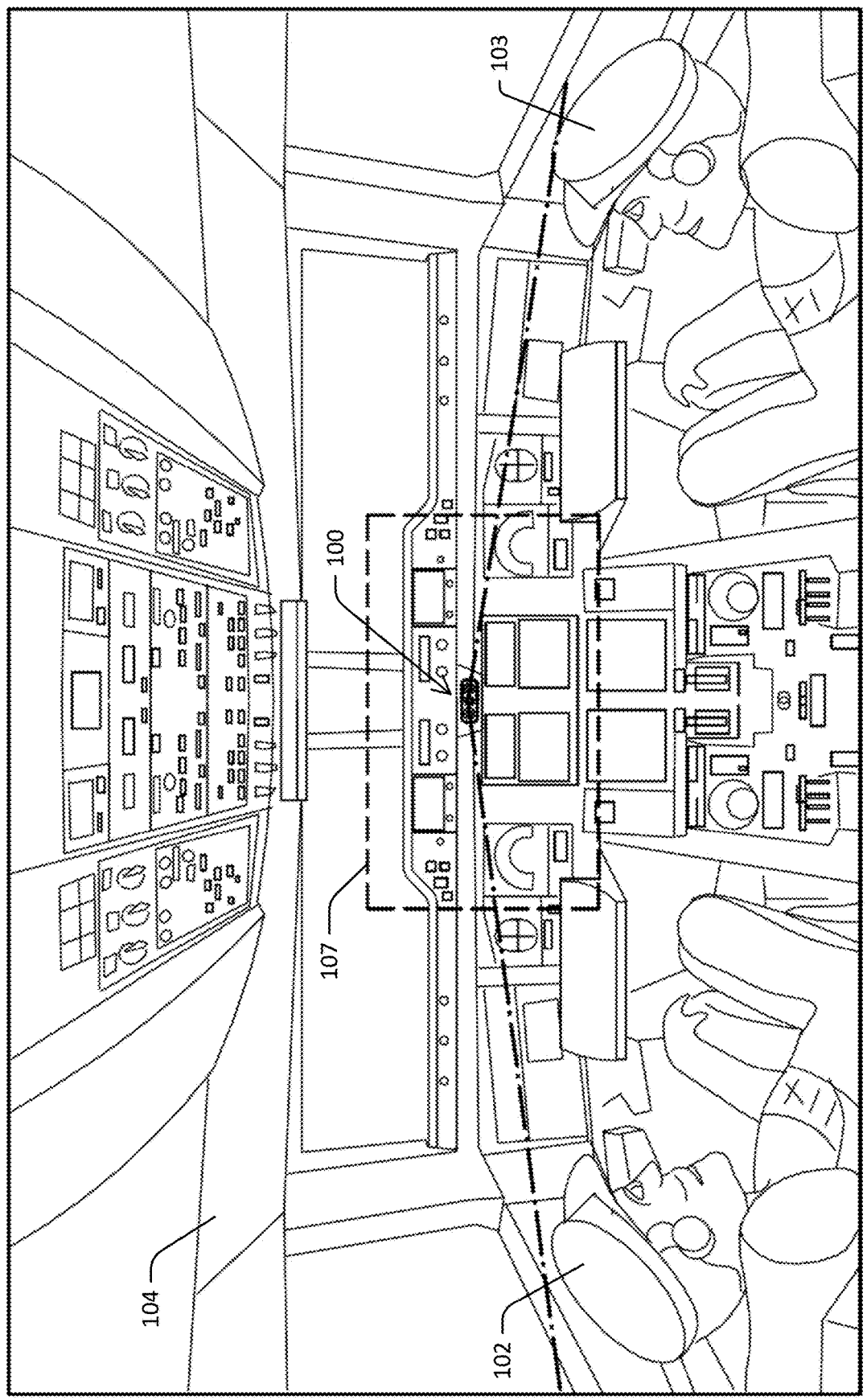
FIG. 1 is a perspective view of the interior of an aircraft cockpit having a pilot monitoring system including a camera and two LED light sources installed therein to monitor both a pilot and co-pilot.
Figure 2:
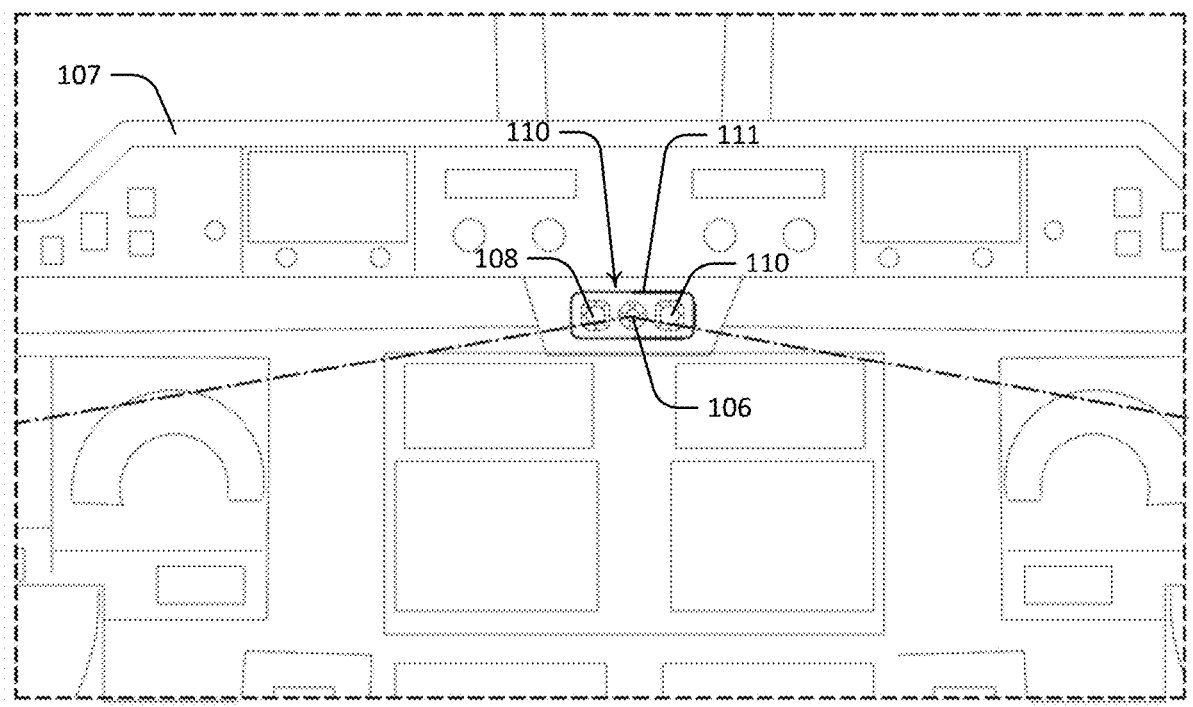
FIG. 2 is a pilot's perspective view of a cockpit instrument panel having the pilot monitoring system of FIG. 1 installed therein.

As best illustrated in FIG. 2, system 100 includes an imaging camera 106 that is positioned on or in the cockpit instrument panel 107 and oriented to capture images of at least the pilot's and/or co-pilot's face in the infrared wavelength range to identify, locate and track one or more human facial features. Camera 106 may also image the pilot's and/or co-pilot's head and body to determine head and body position and movement.

Camera 106 may be a conventional CCD or CMOS based digital camera having a two dimensional array of photosensitive pixels and optionally the capability to determine range or depth (such as through one or more phase detect elements). The photosensitive pixels are capable of sensing electromagnetic radiation in the infrared range. Camera 106 may also be a three dimensional camera such as a time-of-flight camera or other scanning or range-based camera capable of imaging a scene in three dimensions. In other embodiments, camera 106 may be replaced by a pair of like cameras operating in a stereo configuration and calibrated to extract depth. Although camera 106 is preferably configured to image in the infrared wavelength range, it will be appreciated that, in alternative embodiments, camera 106 may image in the visible range.

Referring still to FIG. 2, system 100 also includes a pair of infrared light sources in the form of light emitting diodes (LEDs) 108 and 110, horizontally disposed at respective positions proximate to the camera on cockpit instrument panel 107. LEDs 108 and 110 may be disposed at the same or different distances from camera 106. The positions of LEDs 108 and 110 may be sufficiently close to camera 106 such that they illuminate the pilot/co-pilot in a bright pupil condition. This typically occurs when the LEDs 108 and 110 are located off the camera axis by an angle of less than about 4 degrees when imaging a subject at a distance of about 1 m. In other embodiments, LEDs 108 and 110 may be positioned sufficiently far from camera 106 that they illuminate the pilot/co-pilot in a dark pupil condition.

In further embodiments (not illustrated), only a single LED is used. Also, in some embodiments, more than two light sources may be employed in the system per subject being imaged. In the illustrated embodiments, the first and a second light source each include a single LED. In other embodiments, each light source may each include a plurality of individual LEDs such as a ring of LEDs which can be individually actuated to provide varying degrees of illumination. It will be appreciated that, in other embodiments, LEDs 108 and 110 can be replaced with other types of light source such as Vertical Cavity Surface Emitting Lasers (VCSELs).

LEDs 108 and 110 are adapted to illuminate pilot 102 and/or co-pilot 103 with infrared radiation, during predefined image capture periods when camera 106 is capturing an image, so as to enhance the pilot/co-pilot's face and/or body to obtain high quality images of the pilot/co-pilot's face, facial features and/or body features. Operation of camera 106 and LEDs 108 and 110 in the infrared range reduces visual distraction to the pilot/co-pilot. Operation of camera 106 and LEDs 108, 110 is controlled by an associated controller 112 which comprises a computer processor or microprocessor and memory for storing and buffering the captured images from camera 106.

As best illustrated in FIG. 2, camera 106 and LEDs 108 and 110 may be manufactured or built as a single unit 111 having a common housing. The unit 111 is shown installed in a central region of the cockpit instrument panel 107 and may be fitted during manufacture of the cockpit or installed subsequently as an after-market product. In other embodiments, the pilot monitoring system 100 may include one or more cameras and light sources mounted in any location suitable to capture images of the head or facial features of a pilot, subject and/or crew member in the cockpit.

Figure 3:
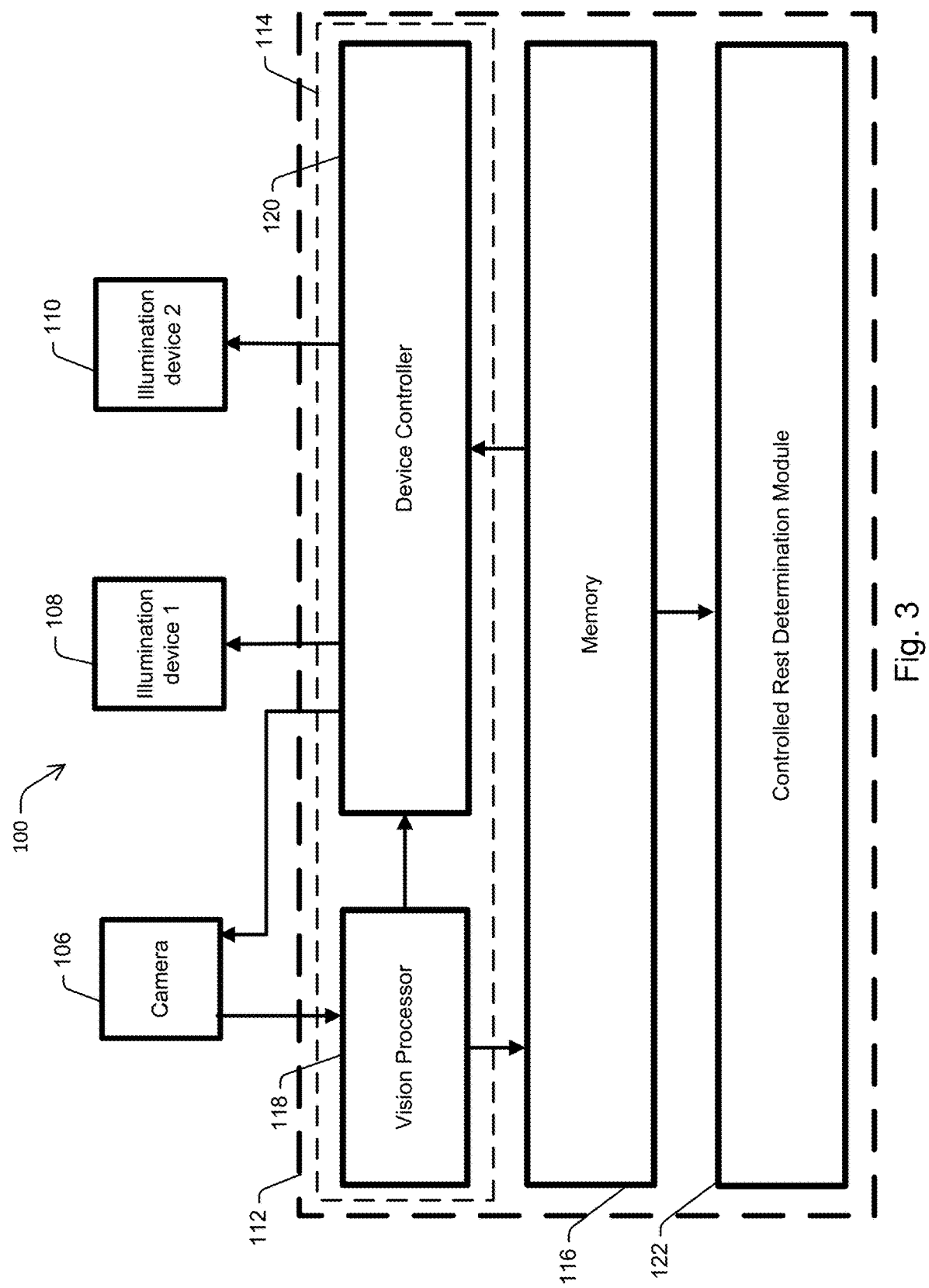
FIG. 3 is a schematic functional view of a pilot monitoring system according to FIGS. 1 and 2.
Figure 4:
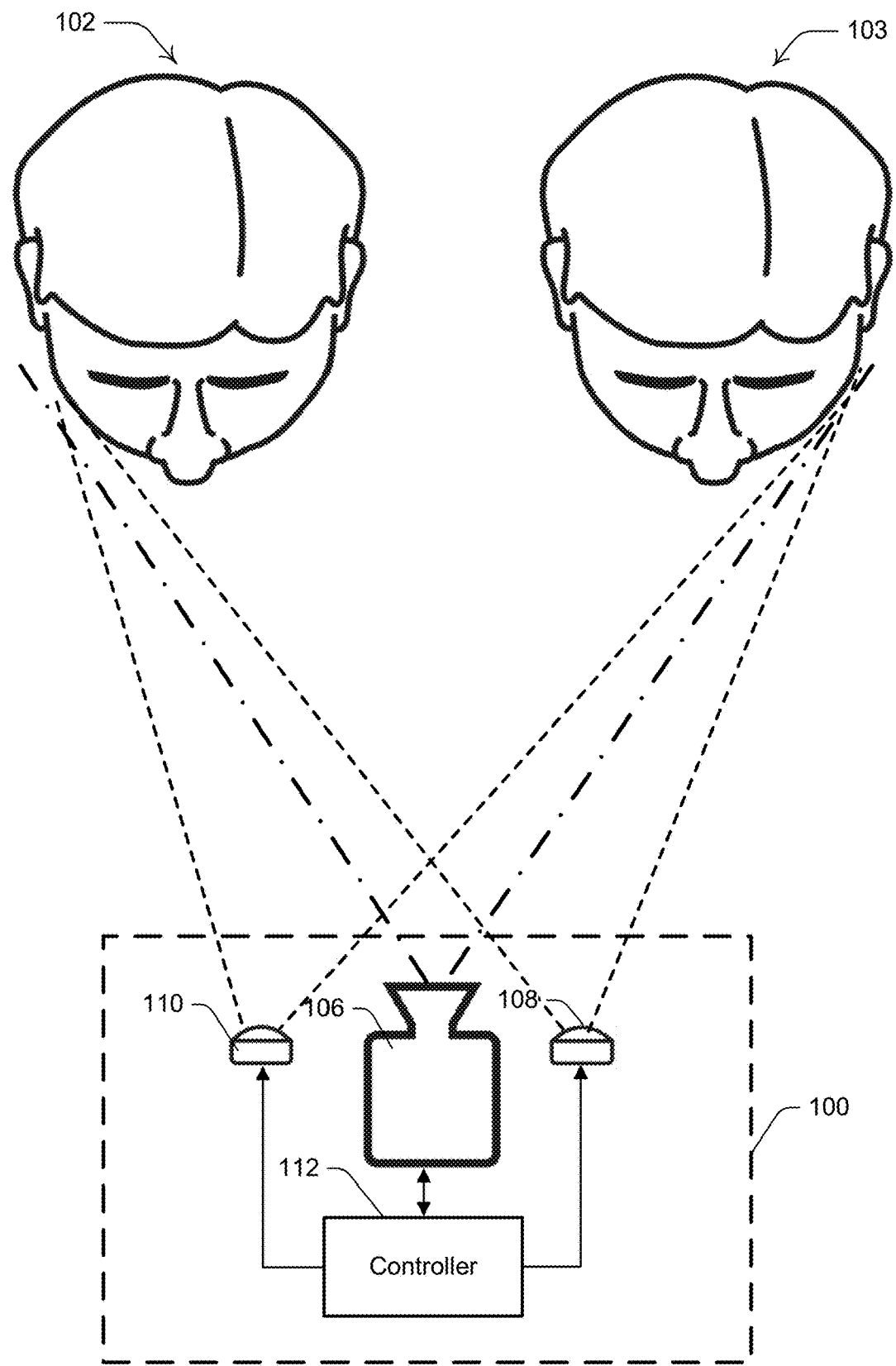
FIG. 4 is a plan view of the pilot monitoring system of FIGS. 1 to 3 showing a camera field of view and an LED illumination field on a subject.

In the embodiment illustrated in FIGS. 1 to 4, system 100 is adapted to simultaneously image and monitor both the pilot 102 and co-pilot 103. This is achieved by positioning the camera 106 in a centrally located position on cockpit instrument panel 107 and camera 106 includes a wide angle lens such that both the pilot 102 and co-pilot 103 are included in the camera field of view. This wide field of view is illustrated in FIG. 4. In this embodiment, only a single camera and illumination system is needed in a cockpit.

In the embodiment of FIGS. 1 to 4, LEDs 108 and 110 are positioned and oriented to image both the pilot 102 and co-pilot 103. However, in some embodiments, additional LEDs may be included to image both the pilot 102 and co-pilot 103. By way of example, system 100 may include a first pair of LEDs located in the instrument panel 107 in front of pilot 102 and a second pair of LEDs located in the instrument panel 107 in front of co-pilot 103.

Turning now to FIG. 3, the functional components of system 100 are illustrated schematically. A system controller 112 acts as the central processor for system 100 and is configured to perform a number of functions as described below. Controller 112 is preferably located within or proximal to the cockpit instrument panel 107 and may be connected to or integral with the aircraft flight management system. In another embodiment, controller 112 may be located within a housing or module together with camera 106 and LEDs 108 and 110. The housing or module is able to be sold as an after-market product, mounted to the cockpit instrument panel and subsequently calibrated for use in the cockpit. In further embodiments, controller 112 may be an external computer or unit such as a personal computer.

Controller 112 may be implemented as any form of computer processing device or portion of a device that processes electronic data, e.g., from registers and/or memory to transform that electronic data into other electronic data that, e.g., may be stored in registers and/or memory. As illustrated in FIG. 3, controller 112 includes a microprocessor 114, executing code stored in memory 116, such as random access memory (RAM), read-only memory (ROM), electrically erasable programmable read-only memory (EEPROM), and other equivalent memory or storage systems as should be readily apparent to those skilled in the art.

Microprocessor 114 of controller 112 includes a vision processor 118 and a device controller 120. Vision processor 118 and device controller 120 represent functional elements which are both performed by microprocessor 114. However, it will be appreciated that, in alternative embodiments, vision processor 118 and device controller 120 may be realized as separate hardware such as microprocessors in conjunction with custom or specialized circuitry.

Vision processor 118 is configured to process the captured images to perform the pilot/co-pilot monitoring; for example to determine a three dimensional head pose, body pose, eye closure and/or eye gaze position of the pilot 102 within the monitoring environment. To determine the eye gaze position, vision processor 118 utilizes one or more eye gaze determination algorithms. This may include, by way of example, the methodology described in Edwards et al. Vision processor 118 may also perform various other functions including determining attributes of the pilot 102 or co-pilot 103 such as blink rate and tracking the pilot's head position and motion, and body position and motion to detect pilot attention, cognitive state/load, sleepiness or other issues that may interfere with the pilot safely operating the aircraft.

The raw image data, gaze position data, eye closure, head pose, body pose and other data obtained by vision processor 118 are stored in memory 116.

Device controller 120 is configured to control camera 106 and to selectively actuate LEDs 108 and 110 in a sequenced manner in sync with the exposure time of camera 106. For example, LED 108 may be controlled to activate during odd image frames and LED 110 is controlled to active during even image frames to perform a strobing sequence. Other illumination sequences may be performed by device controller 120, such as L, L, R, R, L, L, R, R . . . or L, R, 0, L, R, 0, L, R, 0 . . . where "L" represents left mounted LED 108, "R" represents right mounted LED 110 and "0" represents an image frame captured while both LEDs are deactivated. LEDs 108 and 110 are preferably electrically connected to device controller 120 but may also be controlled wirelessly by controller 120 through wireless communication such as Bluetooth™ or WiFi™ communication.

Thus, during operation of aircraft 104, device controller 120 activates camera 106 to capture images of the face of pilot 102 and co-pilot 103 in a video sequence. LEDs 108 and 110 are activated and deactivated in synchronization with consecutive image frames captured by camera 106 to illuminate the pilot/co-pilot during image capture. Working in conjunction, device controller 120 and vision processor 118 provide for capturing and processing images of the pilot/co-pilot to obtain subject state information such as drowsiness, attention, body position and posture, head pose and motion, cognitive state/load and gaze position during an ordinary operation of aircraft 104.

Additional components of the system may also be included within the common housing of unit 111 or may be provided as separate components according to other additional embodiments. In one embodiment, the operation of controller 112 is performed by or integrated into an onboard aircraft computer system such as the flight management system or aircraft interfacing device which is connected to camera 106 and LEDs 108 and 112. By way of example, the aircraft interfacing device may include an Intelisight™ Aircraft Interface Device (AID) developed by Collins Aerospace, which is capable of storing and accessing aircraft data and communications, navigation logging, flight tracking, obtaining weather information and monitoring aircraft health among other things.

Figure 5:
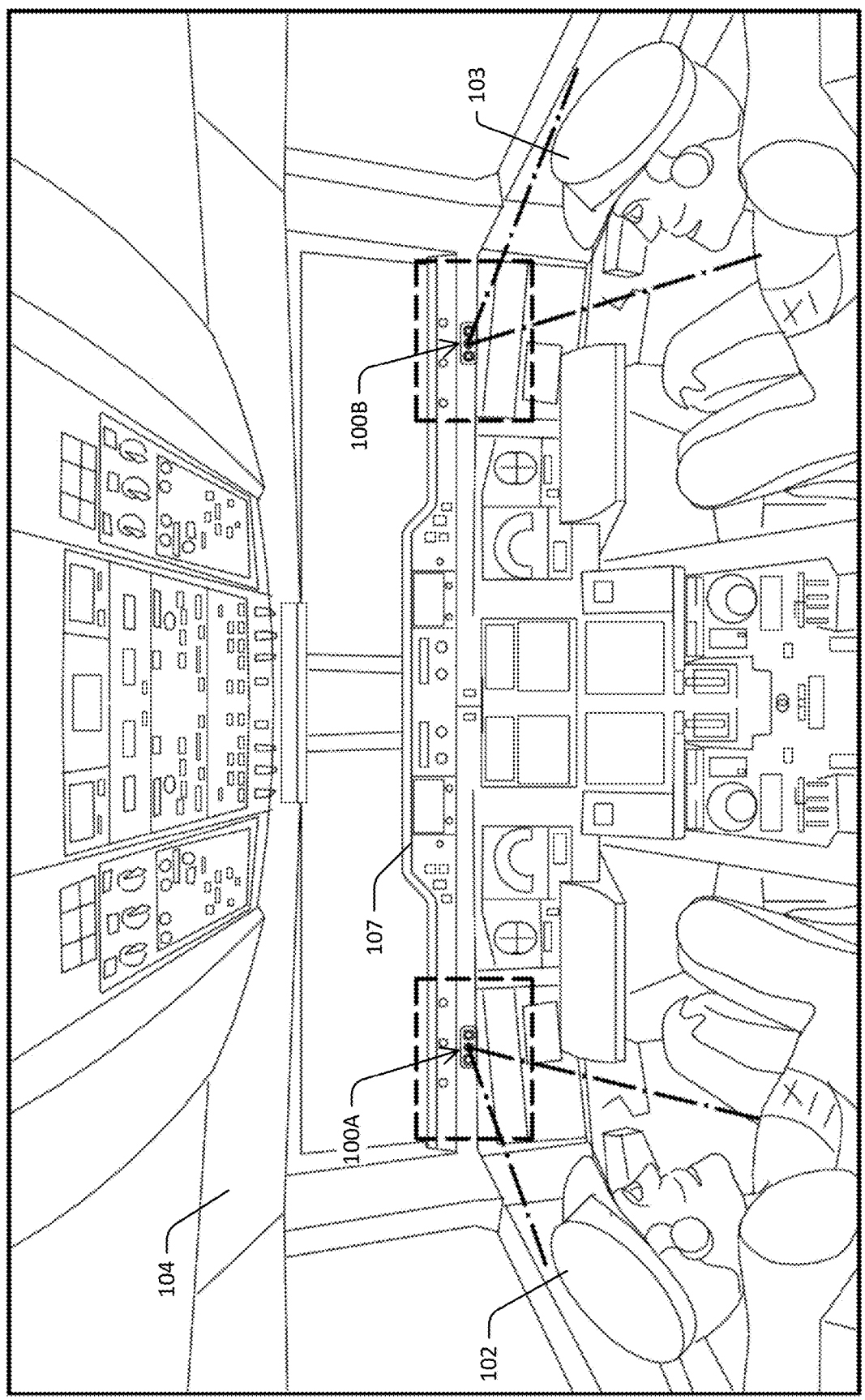
FIG. 5 is a perspective view of the interior of an aircraft cockpit having two pilot monitoring systems, each including a camera and two LED light sources, the pilot monitoring systems being positioned to respectively image a pilot and a co-pilot.
Figure 6:
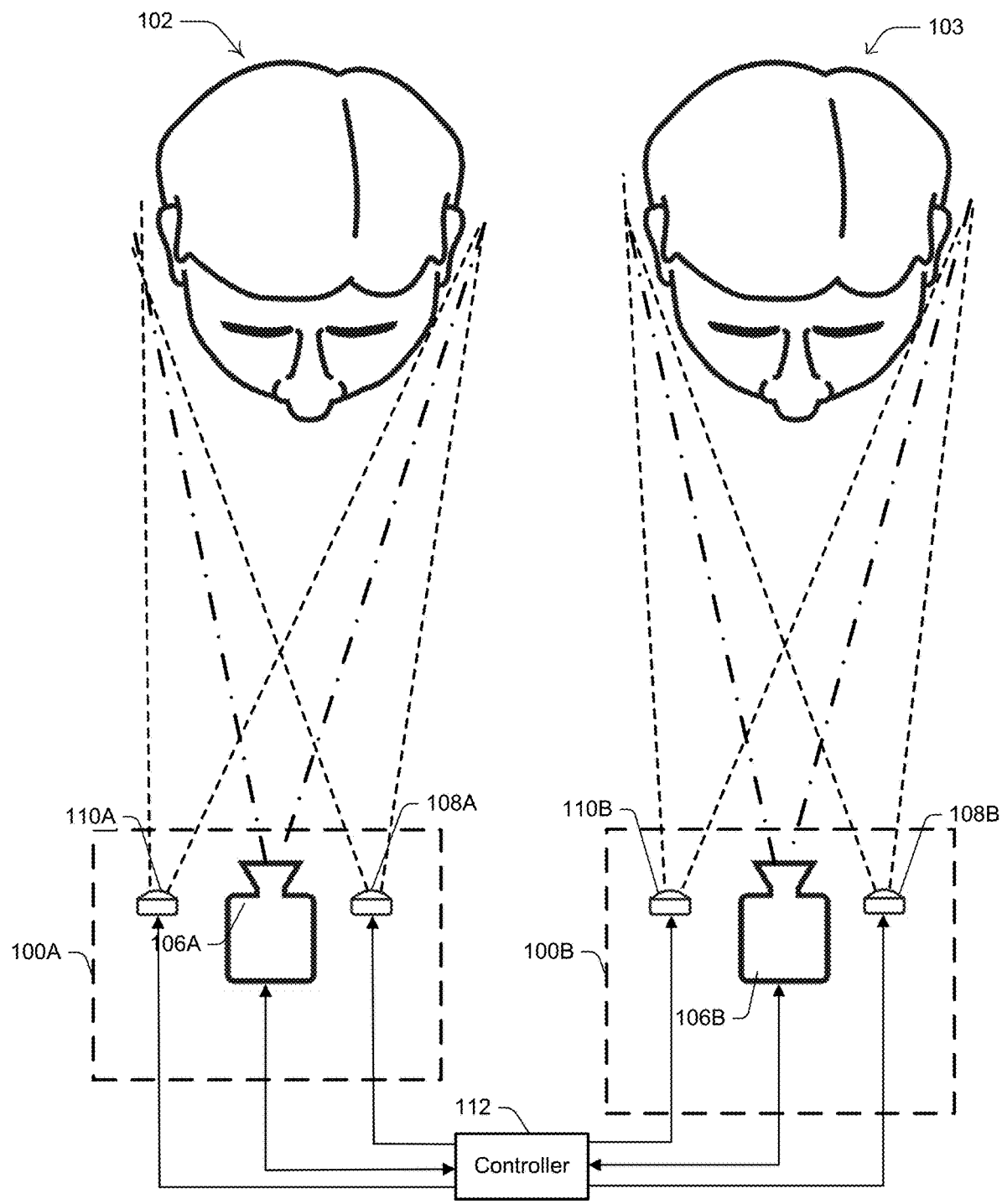
FIG. 6 is a plan view of the pilot monitoring system of FIG. 5 having two systems with respective cameras and LEDs, and showing the cameras' fields of view and LED illumination fields on a pilot and co-pilot.

Referring now to FIGS. 5 and 6, there is illustrated an alternative embodiment in which system 100 includes two subsystems 100A and 100B. The two subsystems 100A and 100B each include respective cameras 106A and 106B and pairs of LEDs 108A, 108B and 110A and 110B. However, the two subsystems 100A and 100B share a common controller 112, which controls the components of each subsystem and performs the image processing of images captured by both cameras 106A and 106B. In other embodiments, the two subsystems include separate controllers that may be integrated into the aircraft's flight management system.

In other embodiments, system 100 may include other cameras positioned to image pilot 102 and/or co-pilot 103. By way of example, one or more cameras may be positioned on or near a ceiling of the cockpit to image pilot 102 and/or co-pilot 103 in a substantially vertically downward direction. Imaging the pilot/co-pilot from this perspective may be useful in more accurately detecting the body pose of the pilot/co-pilot and detect an alertness level of the pilot/co-pilot when in a horizontal resting position in the cabin.

Crew Fatigue Risk Management System

Figure 7:
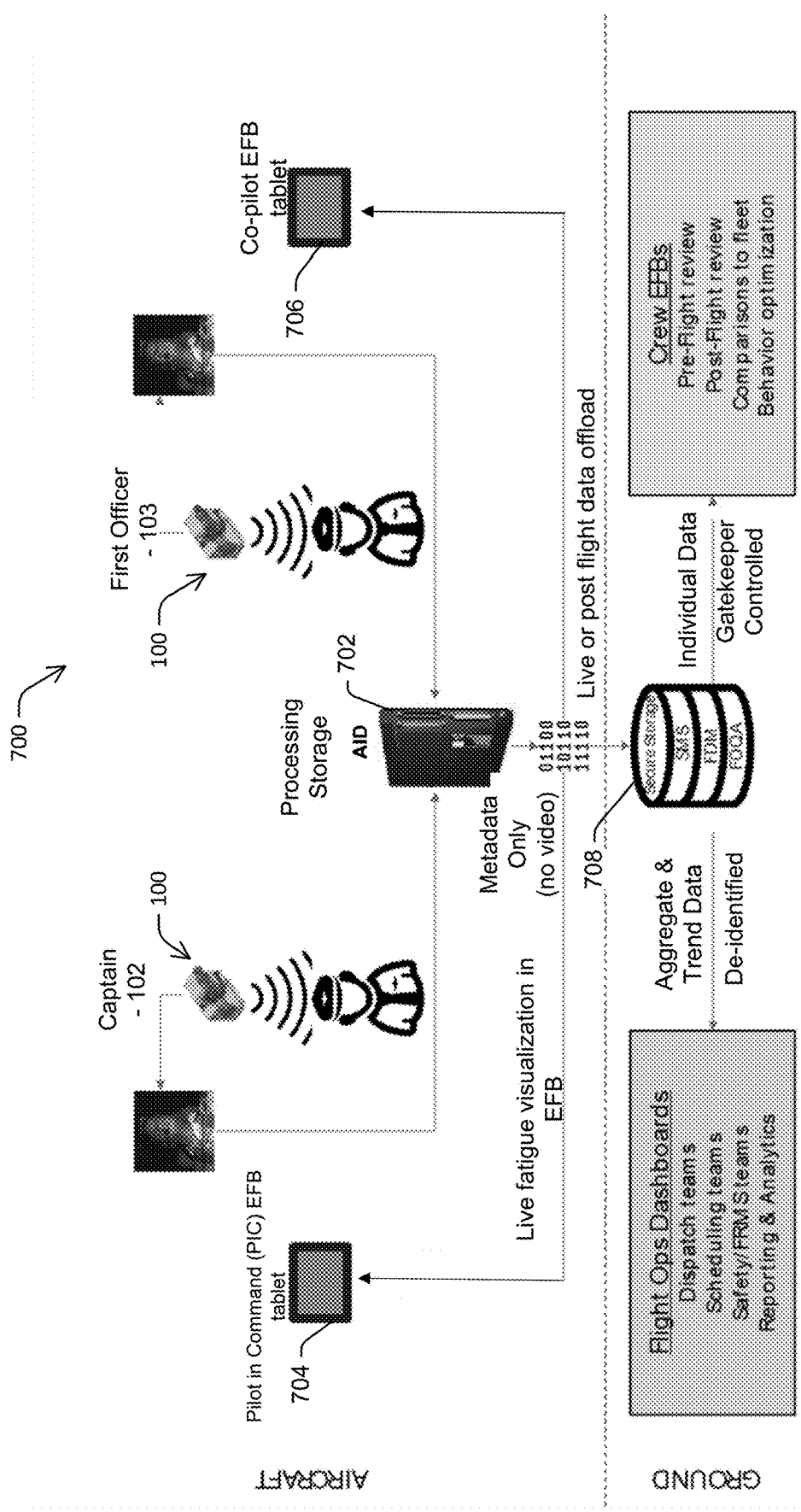
FIG. 7 is a schematic system diagram illustrating a Crew Fatigue Risk Management System that utilises the pilot monitoring system of FIGS. 5 and 6.

Referring now to FIG. 7, the embodiments of system 100 described above are capable of operating as or being used in a Crew Fatigue Risk Management System (CFRMS) 700. CFRMS 700 is capable of performing a pilot monitoring method 800 illustrated in FIG. 8. CFRMS 700 includes a pair of pilot monitoring systems 100 positioned within the aircraft cabin to respectively image the pilot 102 and co-pilot 103. The data obtained from systems 100 may be passed to a central data processing and storage unit 702 located onboard the aircraft for storage, additional processing and decision making. In some embodiments, data processing and storage unit 702 is integral with or leverages controller 112 and memory 116 of systems 100. As mentioned above, in some embodiments, only a single pilot monitoring system 100 may be used to image both pilot 102 and co-pilot 103, as shown in FIGS. 1 to 4.

CFRMS 700 also includes or communicates with one or more Electronic Flight Bags (EFBs) 704 and 706 for displaying data to the pilot 102 and/or co-pilot 130 as described below. EFBs 704 and 706 are electronic information management devices such as tablet computers that helps flight crews perform flight management tasks. Although two EFBs are illustrated, in other embodiments, only a single EFB may be required. In other embodiments, CFRMS 700 includes or communicates with other electronic information management devices such as a cockpit integrated computer.

Figure 8:
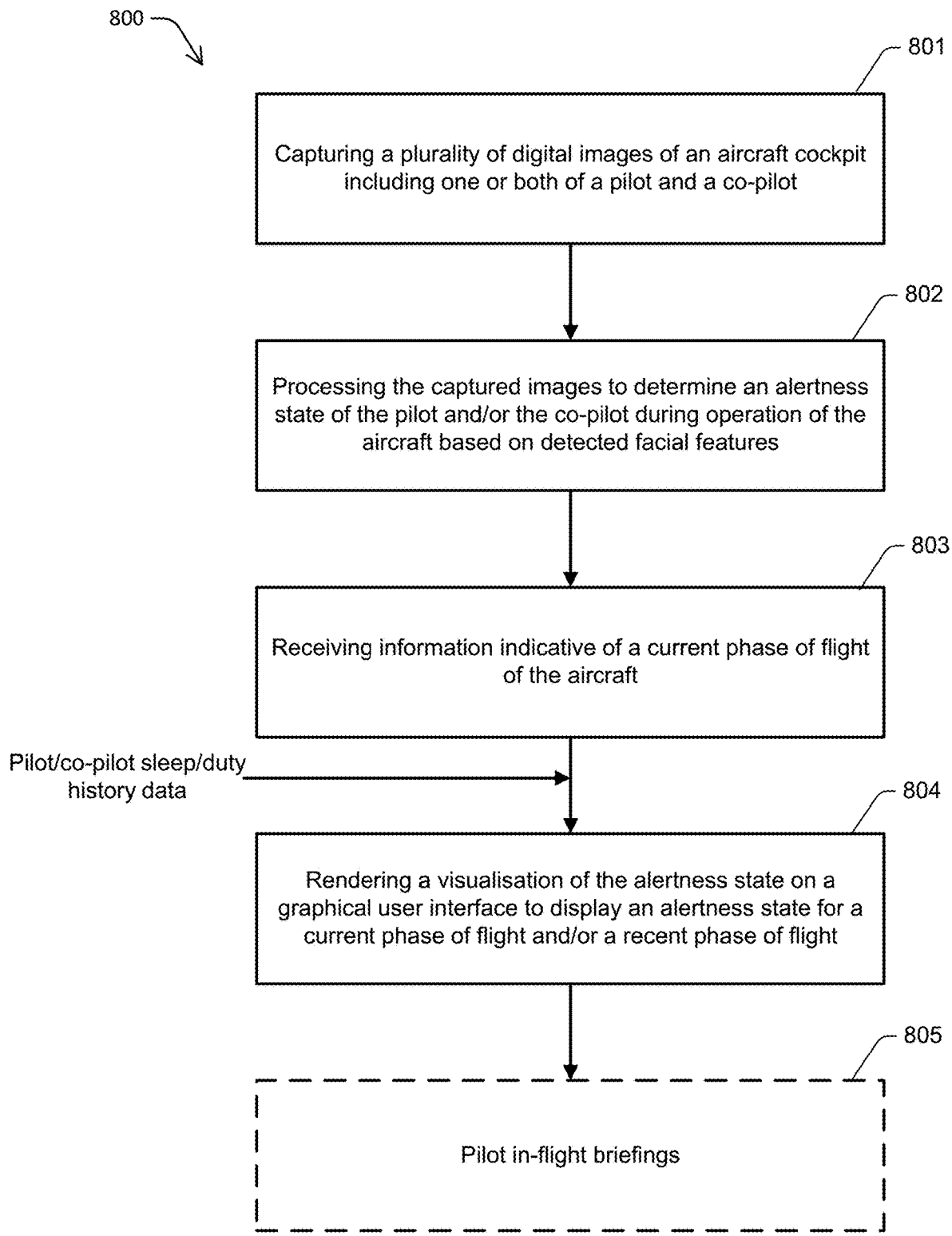
FIG. 8 is a process flow diagram illustrating the primary steps in a pilot monitoring system for monitoring fatigue or alertness of a pilot and/or co-pilot.

Referring now to FIG. 8, at step 801, camera 106 is controlled by device controller 120 to capture a plurality of digital images of the cockpit of aircraft 104 including one or both of the pilot 102 and a co-pilot 103. As mentioned above, camera 106 may be configured to simultaneously image one or both of the pilot 102 and co-pilot 103 using a wide angled lens as per FIGS. 1 to 4. Alternatively, separate systems 100A and 100B with respective cameras may be used to independently image the pilot 102 and co-pilot 103 as per FIGS. 5 and 6. Preferably, both the pilot 102 and co-pilot 103 are imaged either together or independently so as to be able to monitor an attention state of both subjects simultaneously.

Device controller 102 controls camera 106 to capture a sequence of time separated images having a predefined frame rate, exposure period and sensor integration time. Device controller 120 is also configured to control the illumination profile (intensity and pulse time) of LEDs 108 and 110 and/or which LEDs are activated during the image capture periods. By way of example, controller 120 may control LEDs 108 and 110 to illuminate in a strobing sequence to activate on alternate exposure periods to reduce glare effects, as mentioned above. The illumination profile may be selected based on factors such as glare, presence of glasses worn by the pilot or co-pilot, ambient light levels etc.

At step 802, vision processor 118 processes the images captured by camera 106 to determine an alertness state of the pilot 102 and/or the co-pilot 103 during operation of the aircraft based on detected facial and/or body features. Preferably the alertness state of both the pilot 102 and co-pilot 103 are monitored simultaneously where both are present and able to be imaged. Example facial features include nostrils, eyelid contours, pupils, irises, mouth corners and lips. Example body features include, head size, head shape, head orientation, neck shape and position, body shape, body posture, body position, body size, arm position and leg position. These features may be detected by standard image processing techniques such as edge detection, contour detection and contrast detection.

In addition, vision processor 118 may also be configured to determine motion of the pilot 102 and/or co-pilot 103 across a sequence of images and this motion may be used to determine the alertness state. By way of example, vision processor 118 may identify and track a pilot's head motion, arm motion, neck motion, leg motion, body motion, mouth movement and/or change in body posture across a plurality of captured images. Detection of motion such as head nodding, slumped body posture, lack of or slow arm movement may indicate the pilot/co-pilot is in an unconscious or drowsy state. Conversely, regular head turns, arm movement, body position changes, eye movement and/or mouth movement may indicate the pilot/co-pilot is in a highly alert state.

To reduce computational load, in some embodiments, only a subset of the captured images are processed to determine an alertness state. In some embodiments, vision processor 118 filters higher quality images from lower quality images where extraction of facial features is difficult and only process the higher quality images that meet certain criteria.

The alertness state estimation may use the detected facial and/or body features to determine one or more of eye closure frequency and duration, blink rate, mouth movement, head pose and eye gaze direction of one or both eyes. The eye gaze direction may be calculated based on determined regions of interest such as using the method described in PCT Patent Application Publication WO2020/061650 A1 to Edwards and Noble entitled "Driver Attention State Estimation" and assigned to Seeing Machines Limited.

Vision processor 118 may be configured to detect the shape of the pilot/co-pilot's mouth, including lips and tongue, to determine if the pilot/co-pilot is performing action such as yawning, speaking, eating etc. This mouth shape and movement may be combined with other detected face and body features such as eyes and hand/arm gestures to determine overall expression and gestures by the pilot/co-pilot. These may, in turn, be used to determine the alertness level of the pilot/co-pilot.

In some embodiments, vision processor 118 is configured to perform automated lip reading or speech detection based on the detected mouth movement such as lip shape and other face and body features. In these embodiments, vision processor 118 may use a deep learning algorithm such as a convolutional neural network classifier to perform the automated lip reading. In other embodiments, system 100 may include one or more audio sensors located in the cockpit to detect audio signal(s) of the pilot/co-pilot. These audio signal(s) may be used to directly perform automated speech recognition or may be used in conjunction with vision processor 118 to perform audio visual-automated speech recognition in which both audio and visual signals are used to understand what is being spoken.

In some embodiments, vision processor 118 may be capable of using detected mouth movement to determine speech of the pilot 102 and/or co-pilot 103. Where both pilot 102 and co-pilot 103 are imaged simultaneously, vision processor 118 may be capable of detecting a dialogue between pilot 102 and co-pilot 103. Detection of dialogue can be useful in assessing an alertness level, particularly during critical phases of flight.

Some flight regulations stipulate a sterile cockpit in which no non-flight dialogue is allowed under 10,000 feet of altitude to reduce distractions. System 100, with voice recognition and/or lip reading capability, can detect such non-flight dialogue and issue an alert if necessary. Further, it is possible that this restriction of non-flight dialogue may lead to flight crew becoming more fatigued under 10,000 feet due to less stimulus. System 100 is capable of detecting a reduced alertness level of pilot 102 and/or co-pilot 103 and, in response, prompting increased dialogue between the two pilots.

Example alertness states include a drowsiness or consciousness state of the pilot/co-pilot, a cognitive state and/or a level of distraction. The drowsiness state may be based on a detected amount of eye closure and/or blink rate over a period of time, downward eye gaze, downward head movement or nodding head movement and/or body position or posture. The cognitive state and the level of distraction may be based on a detected amount of eye gaze or head glances at different regions of interest such as at specific instruments within instrument panel 107, at the other pilot/co-pilot and/or through cockpit windows. The cognitive state and level of distraction may also be based on detection of mouth movement indicating the pilot/co-pilot talking to others, performing physical actions in the cockpit, getting out of their seat and detection of the current phase of flight. The alertness states may be further characterized based on the detected facial features into states such as a low vigilance drowsy state, asleep state or incapacitated attention state.

The alertness state of one or both of the pilot 102 and co-pilot 103 is monitored continuously or at regular or irregular intervals over time and may be represented by one or more numerical measures that are stored in memory. By way of example, the alertness state of a pilot/co-pilot may be characterized at least in part by a drowsiness measure between 0 and 10, with 0 representing fully asleep and 10 measuring fully alert. Further, the alertness state of a pilot/co-pilot may also be characterized by a distraction level measure between 0 and 10, with 0 representing high distraction and 10 representing low distraction. In some embodiments, the alertness state of a pilot/co-pilot may be characterized at least in part by a measure of Karolinska Sleepiness Scale (KSS) defined in Åkerstedt T, Gillberg M. "*Subjective and objective sleepiness in the active individual*", Int J Neurosc. 1990; 52:29-37. The KSS scale is a subjective 9-point measure of sleepiness (or equivalently "drowsiness") of a subject at a time. One definition of the scale is as follows—1—Extremely alert, 2—Very alert, 3—Alert, 4—Rather alert, 5—Neither alert nor sleepy, 6—Some signs of sleepiness, 7—Sleepiness, but no effort to keep awake, 8—Sleepiness, but some effort to keep awake, and 9—Very sleepy, great effort to keep awake.

Although subjective, a measure of KSS can be characterized in part by objective biometric characteristics measured by system 100 such as eye closure, blink rate, head pose and movement, eye movement and eye gaze, body pose and body movement. In some embodiments, a plurality of these different biometric characteristics are measured independently and combined to produce an overall KSS score or other alertness state characterization.

In other embodiments, the alertness state of one or both of the pilot 102 and co-pilot 103 is characterized at least in part by a drowsiness measure based on a Samn-Perelli Fatigue Scale. This scale is a seven-point Likert-type scale including:

1=fully alert, wide awake
2. Very lively, responsive, but not at peak
3. Okay, somewhat fresh
4. A little tired, less than fresh
5. Moderately tired, let down
6. Extremely tired, very difficult to concentrate
7. Completely exhausted, unable to function effectively.

At step 803, controller 112 receives information indicative of a current phase of flight of the aircraft. This information may be provided automatically to controller 112 by an on-board flight management system which monitors and controls various in-flight tasks and receives input from avionics instruments onboard aircraft 104. The current phase of flight may also be manually input by the pilot 102 or co-pilot 103 or the manual input may serve as a confirmation of a current phase of flight determined by the flight management system. Example phases of flight include taxiing, take-off, climbing, cruise, descent, approach and landing.

The information indicative of a current phase of flight may include an estimated duration of the phase of flight. By way of example, based on the flight plan, the estimated duration of the cruise phase may be six hours.

Although illustrated sequentially, it will be appreciated that step 803 is not dependent on step 802 and, as such, steps 802 and 803 may be performed temporally interchangeably. In some embodiments, steps 802 and 803 are performed simultaneously with each other. In other embodiments, step 803 is performed prior to step 802.

Optionally, CFRMS 700 may receive input indicative of sleep history and/or a recent duty history of pilot 102 and/or co-pilot 103. This data may be input via data processing and storage unit 702, via EFBs 704 and 706 or directly by the pilot/co-pilot via another interface. This sleep/duty history data may be used to augment the visual alertness state determined in step 802 to generate an overall alertness state and/or used to predict a future alertness state of the pilot/co-pilot.

In addition to the inputs described above, the pilot/co-pilot may also be able to provide manual input to module 122. By way of example, a pilot may be able to input their current alertness level or an amount of sleep they had the previous night. This manual input may also include a pilot/co-pilot identifying themselves (e.g. logging in or being uniquely recognized) so that system 100 can load data related to that pilot/co-pilot. In addition, CFRMS 700 may be capable of capturing biometric information about the pilot/co-pilot and the alertness level may be based at least in part on the biometric information.

As mentioned above, in some embodiments, data processing and storage unit 702 utilizes or implements a machine learned classifier algorithm which receives the various inputs and performs a classification to produce an alertness state of the pilot/co-pilot.

At step 804, a visualization of the alertness state is rendered on a graphical user interface visible to pilot 102 and/or co-pilot 103. By way of example, this graphical user interface may be on one or both of EFB 704 and 706 or may be integrated into instrument panel 107. This visualized alertness state provides for displaying the alertness state to pilot 102 and/or co-pilot 103 in real-time during the flight to make in-flight strategic decisions.

Figure 9:
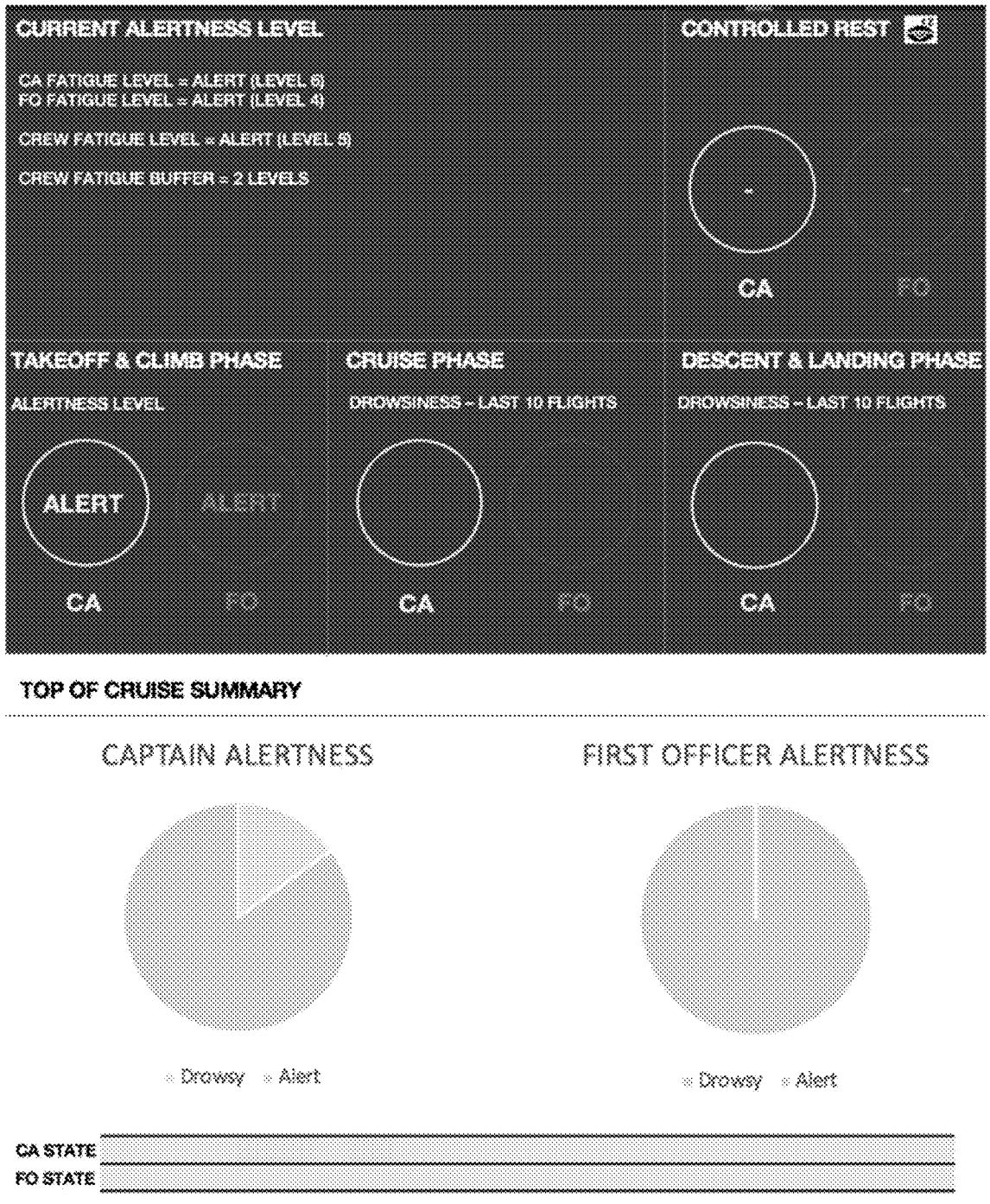
FIG. 9 is a first example dashboard that visualizes an alertness level of a pilot and co-pilot.
Figure 10:
FIG. 10 is a second example dashboard that visualizes an alertness level of a pilot and co-pilot.

The visualization may take the form of a dashboard such as those illustrated in FIGS. 9 and 10. As can be seen, this dashboard includes visual indications of a current fatigue level, alertness state for different phases of flight and an alertness state over the flight duration for both the pilot (Captain) and co-pilot (First Officer). The dashboard also includes visualizations of safety events, instances and durations of drowsiness and sleeping events during different phases of flight and alertness levels of past flights for the pilot/co-pilot.

In conjunction with the visualization of alertness level, method 800 may also include the optional step 805 of issuing one or more pilot briefings to pilot 102 and/or co-pilot 103 during flight the graphical user interface based on the determined alertness state, flight information and optionally in part on the sleep/duty history input. These in-flight briefings may include some or all of the information shown on the dashboards in FIGS. 9 and 10 and/or a current or future predicted fatigue or alertness level of pilot 102 and/or co-pilot 103. The in-flight briefings may include a proposed rest schedule for the pilot 102 and/or co-pilot 103. In some embodiments, the in-flight briefings are issued at different phases of flight such as take-off, cruise and descent.

In some embodiments, the in-flight briefings include fatigue levels at specific intervals such as at touch down, top of cruise, top of descent etc.

In some embodiments, CFRMS 700 is configured to provide alerts to pilot 102 and/or co-pilot 103. These alerts may include visual alerts, audible alerts or audio-visual alerts provided via the graphical user interface or other device within the aircraft cockpit. Haptic feedback may also be provided to the pilot/co-pilot via a seat or wearable device. In some embodiments, CFRMS 700 is capable of determining a minimum alertness threshold for pilot 102 and/or co-pilot 103. This minimum alertness level may be specific to the pilot/co-pilot and may be based on the past sleep/duty history data. Alerts may be issued if that pilot/co-pilot's alertness drops below the minimum alertness threshold or is predicted to drop below this threshold.

As mentioned above, CFRMS 700 may be capable of continuously monitoring the alertness state of pilot 102 and/or co-pilot 103 so as to provide real-time visualisations of alertness level, alerts and in-flight briefings to allow the pilot/co-pilot to make critical flight decisions. CFRMS 700 may suggest fatigue mitigation techniques such as controlled rest events to maintain the pilot/co-pilot's alertness above the threshold.

In some embodiments CFRMS 700 determines a fatigue score of the pilot 102 and/or co-pilot 103 based at least in part on the determined alertness state calculated in step 802. This fatigue score may be visualised on the graphical user interface and included in a dashboard of information displayed to the pilot/co-pilot.

The determination of the pilot/co-pilot alertness level may be determined entirely by vision processor 118 or may be determined in part by data processing and storage unit 702. Unit 702 may include a communications module and be in wireless communication with a remote database 708 accessible by ground crew. This provides access to the ground crew for determining a future flight or rest schedule of the pilot and/or co-pilot. Unit 702 may periodically transmit one or both of the fatigue score or alertness state to database 708. In some embodiments, metadata without video and image content, such as pilot alertness levels, may be transmitted during flight from unit 702 to database 708. Larger datasets including image and video content may be downloaded post flight.

Transmission of data from unit 702 to database 708 allows for post-flight analysis, safety, scheduling and reporting about pilot/co-pilot for future flights.

The CFRMS 700 described above is capable of providing various predictive, proactive and reactive advantages over existing systems/techniques as summarised below.

Predictive
  Historical objective pilot fatigue data from CFRMS 700 can enhance the bio-mathematical model and be considered in previous experience or historical schedules.
  Risk analysis and pairing analysis based on historical objective fatigue data.
  Revised pairings/duty day extensions/departure delays.
Proactive
  Realtime EFB visualization of crew fatigue levels for crew.
  Viewing individual or crew fatigue levels in real-time.
  Alertness score can be used as a decision-making tool.
  Data can be used as input for briefings, including:
    Preflight briefing—consider fatigue scores and aid in crew determination of who takes off;
    Top of Cruise briefing—consider fatigue scores and aid in optimization of rest schedules (long haul), and if crew might consider the need for controlled rest to maintain a fatigue-alertness margin;
    Approach briefing—consider fatigue scores and aid in crew determination of who lands.
  Controlled rest periods to increase alertness at later stages of flight (described below).
Reactive
  In-flight alerting and notification during cruise and/or critical phases of flight.
  In-flight recommendation of controlled rest may be generated based on detected or predicted alertness levels. This is described in more detail below.
  Post-flight automated fatigue reports can be generated to include objective fatigue level throughout flight for the crew.
  Post-flight automated report to indicate if a controlled rest event was used successfully.

By performing the above predictive, proactive and reactive actions, CFRMS 700 is capable of maintaining a predefined appropriate alertness level of one or both pilot 102 and/or co-pilot 103 at specific phases of the flight including Top of Descent (TOD). By way of example, CFRMS 700 may be configured for ensuring that a KSS level of <7 at TOD is achieved for both pilot/co-pilot to ensure a safe descent. This may be performed through the monitoring and alerting of the pilot/co-pilot throughout flight when alertness drops, as well as management of controlled rest periods as described below.

Figure 11:
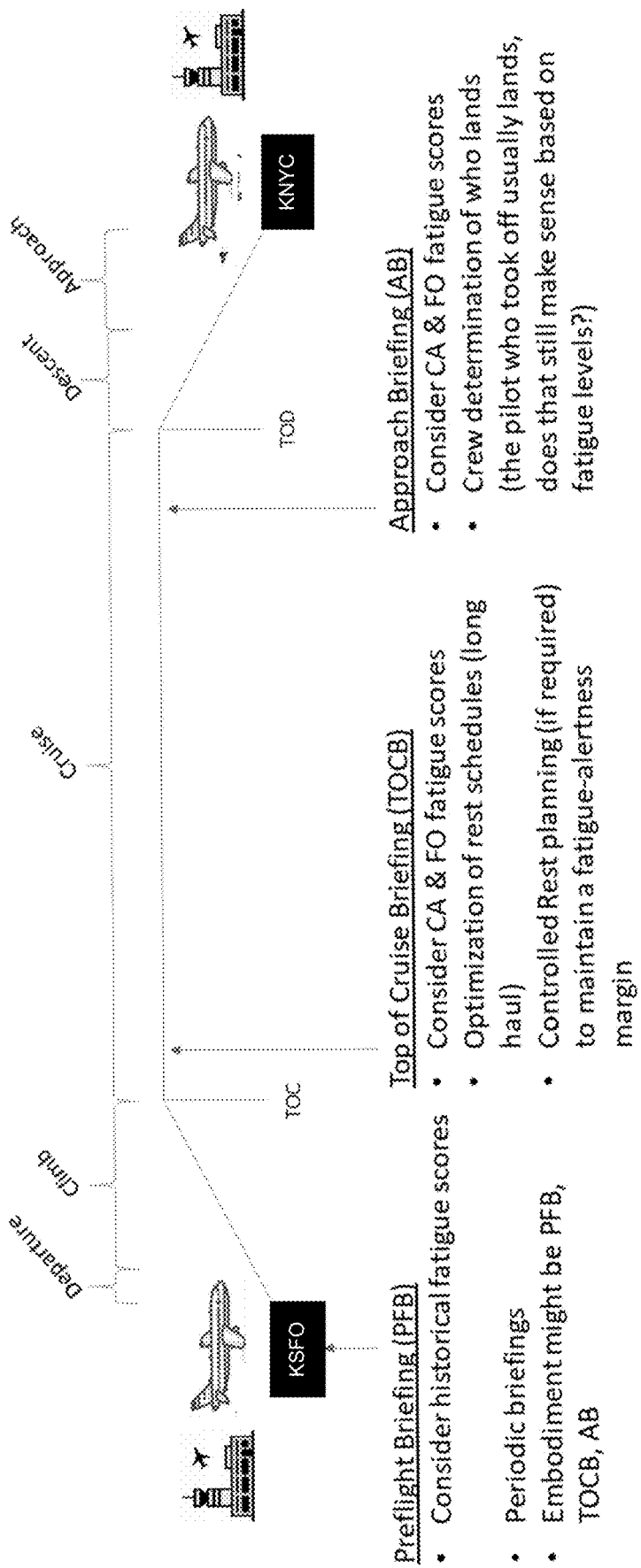
FIG. 11 is a schematic of proactive briefings that can be generated from the Crew Fatigue Risk Management System of FIG. 7.
Figure 12:
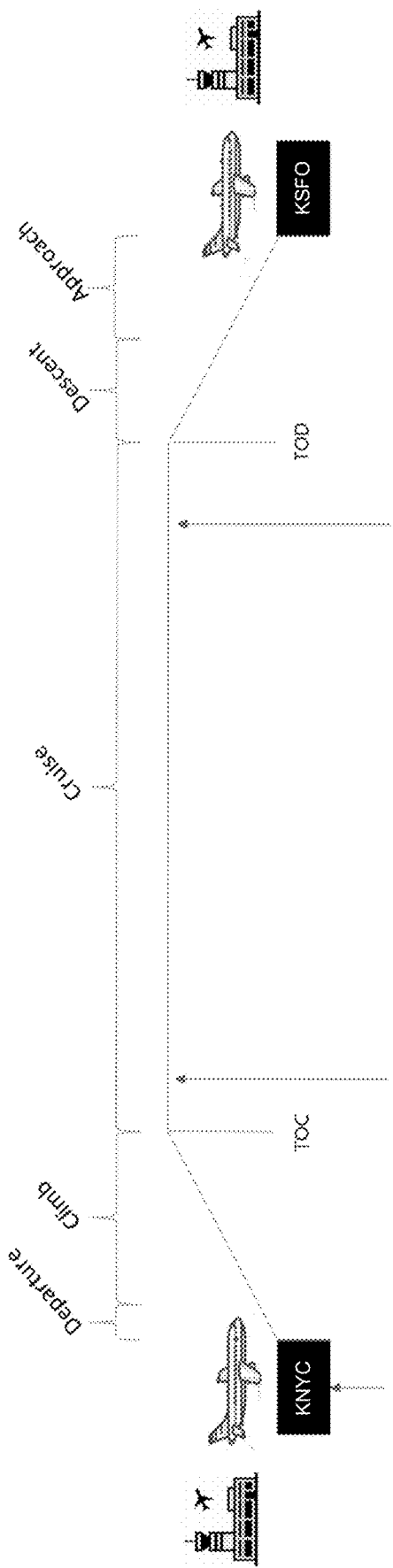
FIG. 12 is a schematic of reactive actions that can be taken from the Crew Fatigue Risk Management System of FIG. 7.

A schematic of proactive briefings that can be generated from CFRMS 700 is illustrated in FIG. 11. A schematic of reactive actions that can be taken from CFRMS 700 is illustrated in FIG. 12.

Controlled Rest Determination

Figure 13:
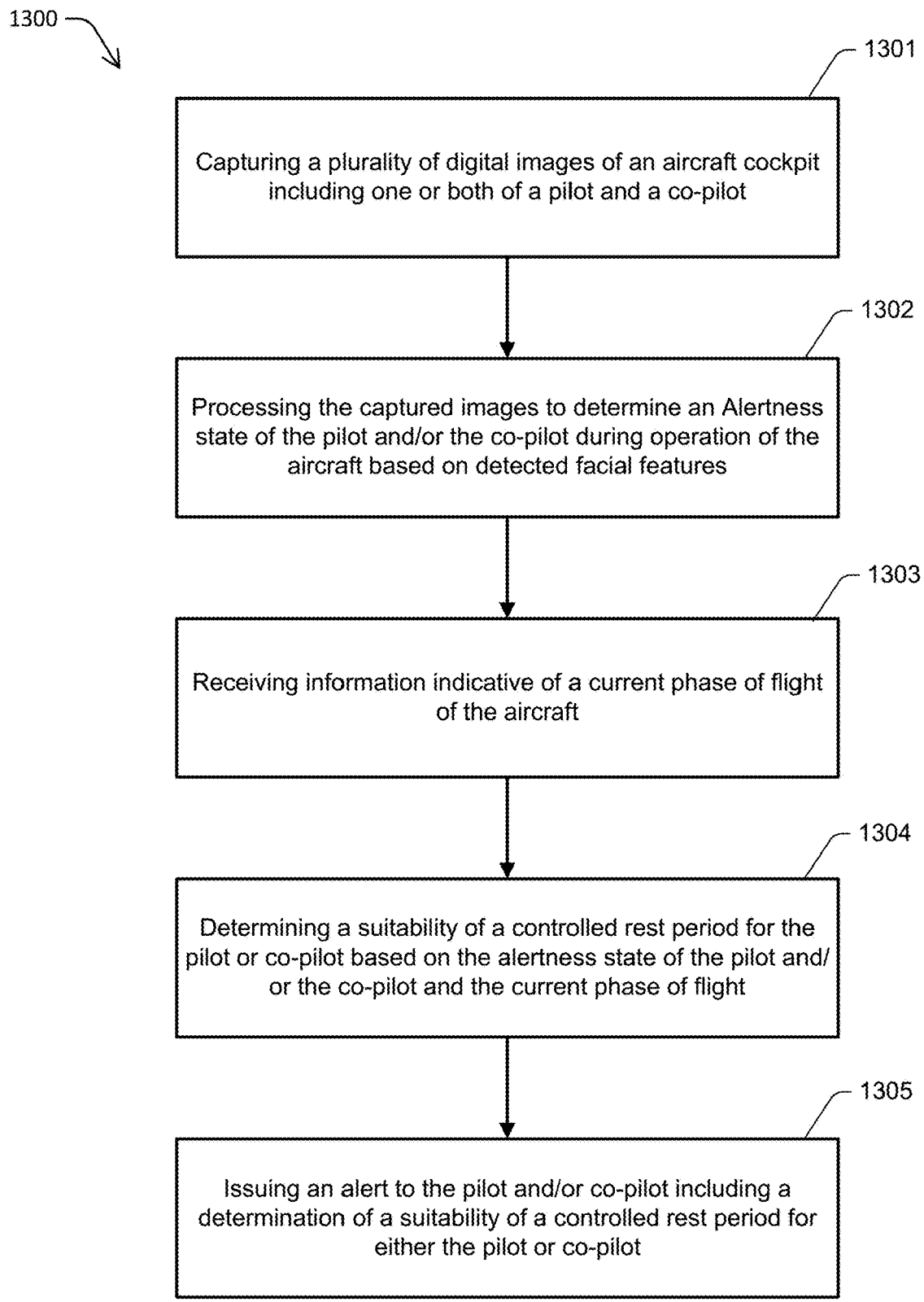
FIG. 13 is a process flow diagram illustrating the primary steps in a pilot monitoring method for determining a suitability of a controlled rest period for a pilot and/or co-pilot.

Referring now to FIG. 13, the embodiments of system 100 described above are capable of performing a pilot monitoring method 1300 for determining suitable periods of controlled rest.

At step 1301, camera 106 is controlled by device controller 120 to capture a plurality of digital images of the cockpit of aircraft 104 including one or both of the pilot 102 and a co-pilot 103. As mentioned above, camera 106 may be configured to simultaneously image one or both of the pilot 102 and co-pilot 103 using a wide angled lens as per FIGS. 1 to 4. Alternatively, separate systems 100A and 100B with respective cameras may be used to independently image the pilot 102 and co-pilot 103 as per FIGS. 5 and 6. Preferably, both the pilot 102 and co-pilot 103 are imaged either together or independently so as to be able to monitor an attention state of both subjects simultaneously.

Device controller 120 is also configured to control the illumination profile (intensity and pulse time) of LEDs 108 and 110 and/or which LEDs are activated during the image capture periods.

At step 1302, vision processor 118 processes the images captured by camera 106 to determine an alertness state of the pilot 102 and/or the co-pilot 103 during operation of the aircraft based on detected facial and/or body features. This includes performing the various analysis described above in relation to step 802. Preferably the alertness state of both the pilot 102 and co-pilot 103 are monitored simultaneously where both are present and able to be imaged. Example facial features include nostrils, eyelid contours, pupils, irises, mouth corners and lips. Example body features include, head size, head shape, head orientation, neck shape and position, body shape, body posture, body position, body size, arm position and leg position. These features may be detected by standard image processing techniques such as edge detection, contour detection and contrast detection.

In addition, vision processor 118 may also be configured to determine motion of the pilot 102 and/or co-pilot 103 as described above and this motion may be used to determine the alertness state.

The alertness state estimation may use the detected facial and/or body features to determine one or more of eye closure frequency and duration, blink rate, mouth movement, head pose and eye gaze direction of one or both eyes. The eye gaze direction may be calculated based on determined regions of interest such as using the method described in PCT Patent Application Publication WO2020/061650 A1 to Edwards and Noble entitled "Driver Attention State Estimation" and assigned to Seeing Machines Limited.

Vision processor 118 may be configured to detect the shape of the pilot/co-pilot's mouth, including lips and tongue, to determine if the pilot/co-pilot is performing action such as yawning, speaking, eating etc., as mentioned above.

In some embodiments, vision processor 118 is configured to perform automated lip reading or speech detection based on the detected mouth movement such as lip shape and other face and body features.

Example alertness states include a drowsiness or consciousness state of the pilot/co-pilot, a cognitive state and/or a level of distraction. The drowsiness state may be based on a detected amount of eye closure and/or blink rate over a period of time, downward eye gaze, downward head movement or nodding head movement and/or body position or posture. The cognitive state and the level of distraction may be based on a detected amount of eye gaze or head glances at different regions of interest such as at specific instruments within instrument panel 107, at the other pilot/co-pilot and/or through cockpit windows. The cognitive state and level of distraction may also be based on detection of mouth movement indicating the pilot/co-pilot talking to others, performing physical actions in the cockpit, getting out of their seat and detection of the current phase of flight. The alertness states may be further characterized based on the detected facial features into states such as a low vigilance drowsy state, asleep state or incapacitated attention state.

As mentioned above, the alertness state of one or both of the pilot 102 and co-pilot 103 is monitored over time and may be represented by one or more numerical measures that are stored in memory such as a drowsiness measure and/or distraction level measure between 0 and 10. The alertness state of a pilot/co-pilot may be characterized at least in part by a measure of the KSS scale.

At step 1303, controller 112 receives information indicative of a current or future phase of flight of the aircraft similar in nature to the information obtained in step 803 described above. This information may be provided automatically to controller 112 by an on-board flight management system which monitors and controls various in-flight tasks and receives input from avionics instruments onboard aircraft 104. The current or future phase of flight may also be manually input by the pilot 102 or co-pilot 103 or the manual input may serve as a confirmation of a current phase of flight determined by the flight management system. Example phases of flight include taxiing, take-off, climbing, cruise, descent, approach and landing.

Although illustrated sequentially, it will be appreciated that step 1303 is not dependent on step 1302 and, as such, steps 1302 and 1303 may be performed temporally interchangeably. In some embodiments, steps 1302 and 1303 are performed simultaneously with each other. In other embodiments, step 1303 is performed prior to step 1302.

In some embodiments, system 100 is only activated during a non-critical phase of flight such as during cruising and does not need to know any information regarding the phase of flight.

At step 1304, controller 112 inputs the alertness state of the pilot 102 and/or the co-pilot 103 and the current phase of flight to a controlled rest determination algorithm to determine a suitability of a controlled rest period for the pilot or co-pilot. This determination may be performed by a controlled rest determination module 122 as part of microprocessor 114. Like, vision processor 118 and device controller 120, controlled rest determination module 122 represents a functional element performed by microprocessor 114. However, it will be appreciated that, in alternative embodiments, controlled rest determination engine 122 may be realized as separate hardware such as microprocessors in conjunction with custom or specialized circuitry.

By way of example, module 122 may determine that pilot 102 has an alertness level (based on the KSS scale) of 2 (very alert) while co-pilot 103 has an alertness level (based on the KSS scale) of 8 (sleepiness, but some effort to keep awake). If the current phase of flight is commencement of the cruise phase, module 122 may make a determination that co-pilot 103 should have a controlled rest of 30 minutes in the next 3-4 hours but no later than 1 hour prior to top of descent. A number of rules and/or thresholds like this can be preconfigured into module 122 and system 100 may continue to monitor the alertness state of pilot/co-pilot throughout the flight.

The determination performed by controlled rest determination module 122 may include a suggested time for the pilot 102 or co-pilot 103 to take a controlled rest and a suitable duration for the controlled rest. This determination may also include a suggestion that the pilot 102 or co-pilot 103 should not have a controlled rest. In some cases, the determination may be that no period of controlled rest is necessary or appropriate based on the detected alertness level and/or phase of flight.

By way of example, the determination by module 122 may specify a time for a controlled rest of a specific time period during the cruise phase but not later than one hour before top of descent. Many regulators recommend approximately 30-45 minutes of controlled rest followed by 20-30 minutes of recovery time to account for sleep inertia.

The determination at step 1304 preferably includes an analysis of the alertness state of both the pilot 102 and co-pilot 103 as well as the availability of cabin crew to check on the cockpit during a controlled rest period, where that is permitted by the relevant regulator, and with the aircraft operator's policy on controlled rest.

Where appropriate permission is sought by pilots and aircraft operators, controller 112 may also be configured to receive input indicative of a sleep history and/or a recent duty history of the pilot 102 and/or co-pilot 103 as an input to the controlled rest determination algorithm. System 100 is configured to have strict privacy protocols so that this personal data is tightly controlled and only accessed by the system itself or authorized persons. This historical data can be used to predict a likely future attention state of the pilot 102 or co-pilot 103 in determining the suitability of a controlled rest period and duration for the pilot 102 or co-pilot 103. For example, if it is known that a pilot has had ample rest/sleep in the 24 hours prior to flight and has not had any duty periods in the 24 hours prior to flight, that could inform the controlled rest determination algorithm relative to knowing that the pilot had the minimum required rest/sleep in the prior 24 hour period, and also performed the maximum duty in the prior 24 hours. Based on the above, the controlled rest determination algorithm can more accurately determine the urgency and confidence level of the controlled rest, and the priority in the event that the pilot and co-pilot require controlled rest on the same flight. Historic data might also include an estimation of the pilot's body clock, which can then predict when their "Window of Circadian Low" (WOOL) will be, which can impact the effectiveness of controlled rest on their sleep recovery (e.g. a 40 minute nap during a pilot's WOOL is more productive than a 40 minute nap outside of their WOOL).

A period of sleep is characterized as occurring in a sequence of stages which are distinguishable by monitoring brain activity and eyelid motion. Stage 1 or 'drowsy' sleep usually occurs during the transition from waking to sleep. This is followed by Stage 2 or 'shallow' sleep and then by Stages 3 & 4 or 'deep' sleep also described as 'slow wave sleep'. This deep sleep may begin within half an hour of falling asleep and its duration is influenced by the length of prior wakefulness. Thereafter, an uninterrupted period of sleep will be cyclic with further but shorter periods of deep sleep separated by shallow sleep.

Waking from sleep means that a degree of 'sleep inertia' occurs. Sleep inertia may be defined as a transitory period of impaired performance and alertness which occurs during the period immediately after waking up. The duration of sleep inertia appears to be influenced by the amount of sleep deficit prior to a nap, the time of day that the nap is taken, and the duration of the nap. It is also likely to be affected by individual susceptibility to its effects. It may significantly affect the ability of a pilot, who has just woken, to effectively perform their normal duties, and a period of time free of both duties and briefing must follow any period of actual sleep. As such, knowing a pilot/co-pilots recent sleep and history can help to improve the estimation of the pilot/co-pilot's actual attention state (not just their alertness state).

The determination of an optimum controlled rest duration at step 1304 may take into account two factors: (1) the duration and magnitude of sleep inertia; and (2) the duration and extent of the beneficial effects on alertness and performance. Whilst the adverse effects of sleep inertia are smaller following short naps (e.g. 10 minutes), the long-term rest benefits of longer naps (e.g. 40-60 minutes) is greater. However, this duration must be balanced with the fact that longer periods of sleep generally give rise to more severe sleep inertia, which adds to the recovery time before a pilot/co-pilot is fully alert. The controlled rest determination algorithm calculates a suggested duration of the controlled rest based on the detected alertness state, available safe time based on phase of flight and the amount of past rest and work the pilot/co-pilot has had.

In some embodiments, system 100 includes or is adapted to receive information from additional hardware that monitors biometric information of the pilot 102 and/or co-pilot 103. In these embodiments, step 1304 may include module 122 receiving biometric information of the pilot 102 and/or co-pilot 103 from a biometric reader device to augment the alertness state data obtained in step 1302 to better understand the true attention state of the pilot/co-pilot. By way of example, the biometric information may include a signal indicative of brain activity received from an electroencephalography (EEG) device connected to the pilot 102 and/or co-pilot 103. The biometric information may include heart rate signal from a heart rate monitor connected to the pilot 102 and/or co-pilot 103 such as an Electrocardiography (ECG) device. The biometric information may include a signal indicative of a breathing rate obtained from a respiratory rate monitor. These biometric inputs will only be provided where non-invasive technology is available, where pilot acceptance is received to use the inputs and under appropriate aviation regulations.

This biometric information may be fed to the controlled rest determination module 122 for making the determination of suitability of a controlled rest period.

In some embodiments, the controlled rest determination module 122 utilized in step 1304 makes use of machine learning to determine an optimum time and duration for a controlled rest. This machine learning may take as inputs, the current or future phase of flight as determined at step 1303, the current alertness state of the pilot 102 and/or co-pilot 103 determined at step 1302, biometric information of the pilot/co-pilot and optionally also historical sleep and duty data of the pilot 102 and/or co-pilot 103.

Finally, at step 1305, controller 112 issues an audio, visual or audiovisual alert to the pilot 102 and/or co-pilot 103 and/or cabin crew based on the determination in step 1304. The alert includes an indication of the determination of the suitability of and/or a type of a controlled rest period for either the pilot or co-pilot during a suitable phase of flight. By way of example, this alert may include a visual indication displayed on a display screen of instrument panel 107, or to the pilot's personal Electronic Flight Bag (EFB) device. The alert may include a duration and/or time window in which the controlled rest should be taken and/or a type of controlled rest. By way of example, controller 112 may issue an alert suggesting a pilot take an in-seat controlled rest of no more than 30 minutes at least an hour prior to top of descent. Another type of controlled rest might be for the pilot to sleep horizontally on a crew bed onboard the aircraft.

The cabin crew outside the cockpit may also be alerted via a signal transmitted to a cabin crew notification system/device. Similarly, if the aircraft has an in-aircraft crew rest facility, an alert may be transmitted to that facility to alert other members of the flight crew who may be resting. The alert may also be transmitted wirelessly from the aircraft to a ground terminal to alert a dispatch, safety or operations member for awareness, decision making, or for record keeping and safety improvement purposes.

Figure 14:
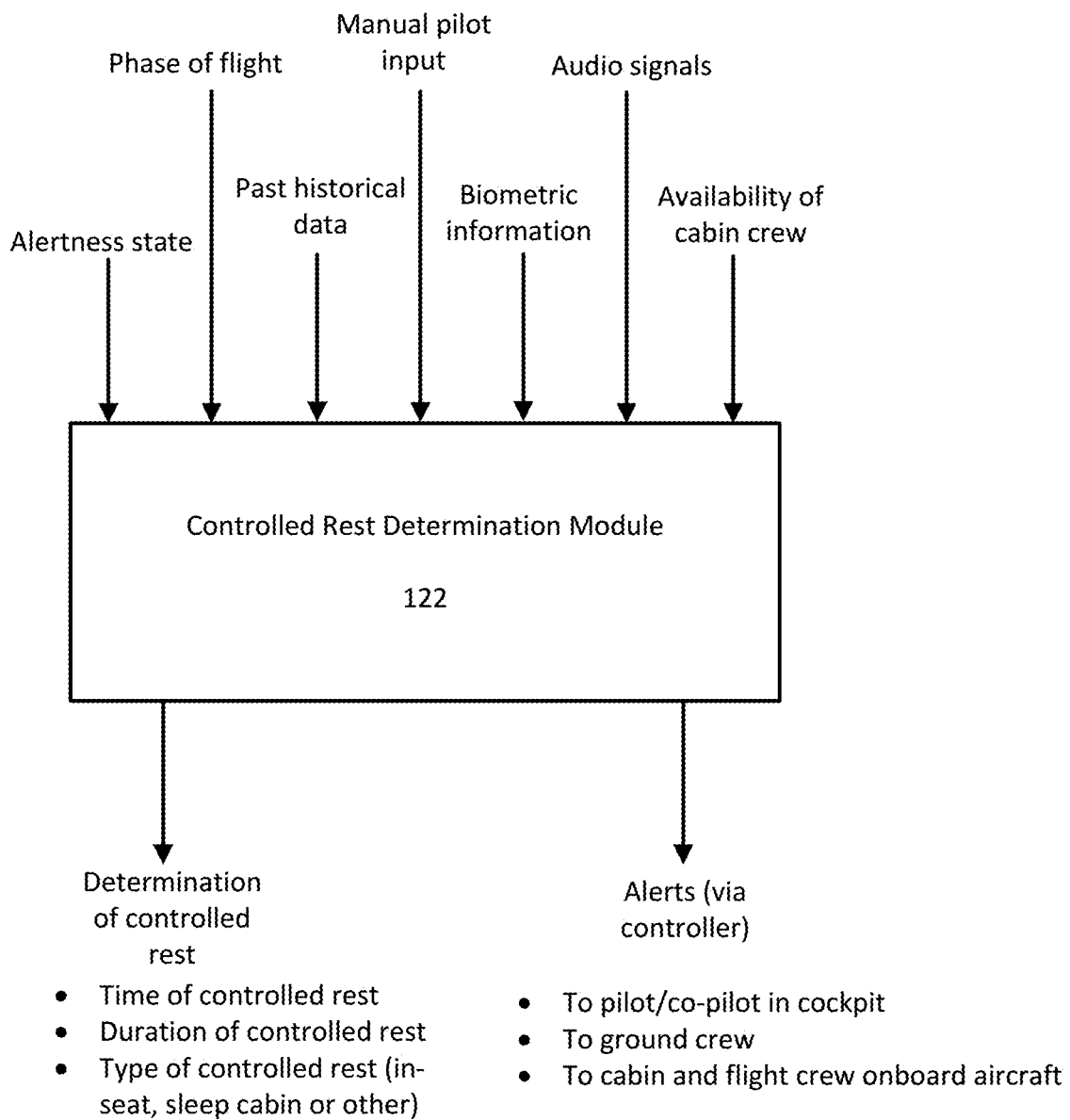
FIG. 14 is a schematic illustration of a controlled rest determination module showing possible inputs and outputs.

Referring to FIG. 14, there is illustrated schematically the controlled rest determination module 122 and the various inputs and outputs that may be fed to/from the module. This illustrates that, in addition to the inputs described above, the pilot/co-pilot may also be able to provide manual input to module 122. By way of example, a pilot may be able to input their current alertness level or an amount of sleep they had the previous night. This manual input may also include a pilot/co-pilot identifying themselves (e.g. logging in) so that system 100 can load data related to that pilot/co-pilot.

As mentioned above, in some embodiments, controlled rest determination module 122 utilizes or implements a machine learned classifier algorithm which receives the various inputs and performs a classification to produce the determination of controlled rest and alerts.

Different types of controlled rest may be implemented. The controlled rest event may be performed "in-seat" where the pilot/co-pilot has a sleep in their seat within the cockpit. The controlled rest event may also be performed as a "single-pilot" event in which the resting pilot/co-pilot has a sleep in a bed such as in a crew rest area of the aircraft. A sleep horizontally in a bed typically provides for a better quality rest.

In addition to monitoring a pilot and/or co-pilot for determining suitable periods of controlled rest, system 100 is also capable of monitoring pilots/co-pilots during periods of controlled rest to ensure the resting pilot/co-pilot has an appropriate controlled rest and that the non-resting pilot/co-pilot is adequately attentive to control the aircraft and monitor the flight path.

Figure 15:
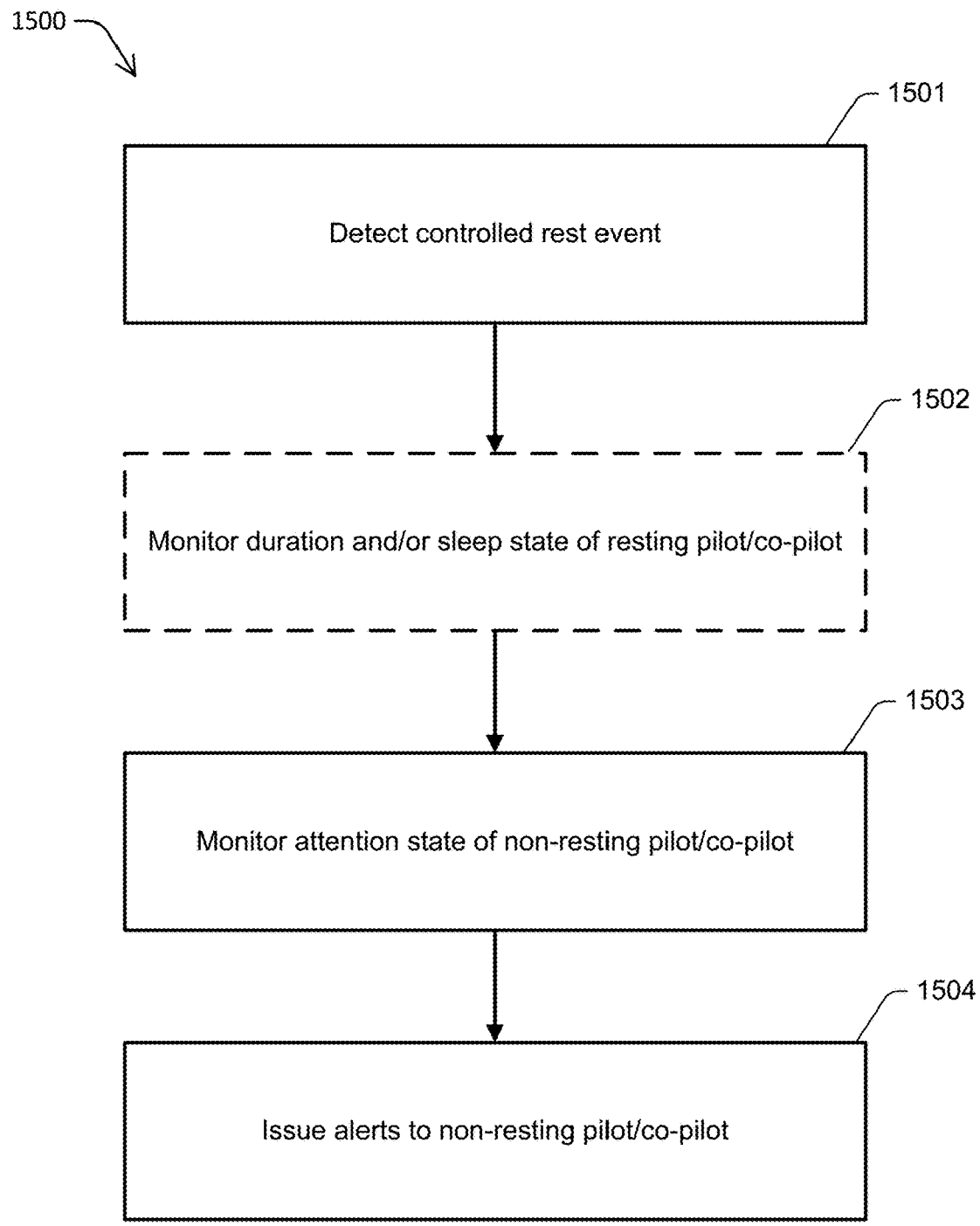
FIG. 15 is a process flow diagram of a pilot monitoring method for monitoring a pilot/co-pilot during a period of controlled rest.
Figure 16:
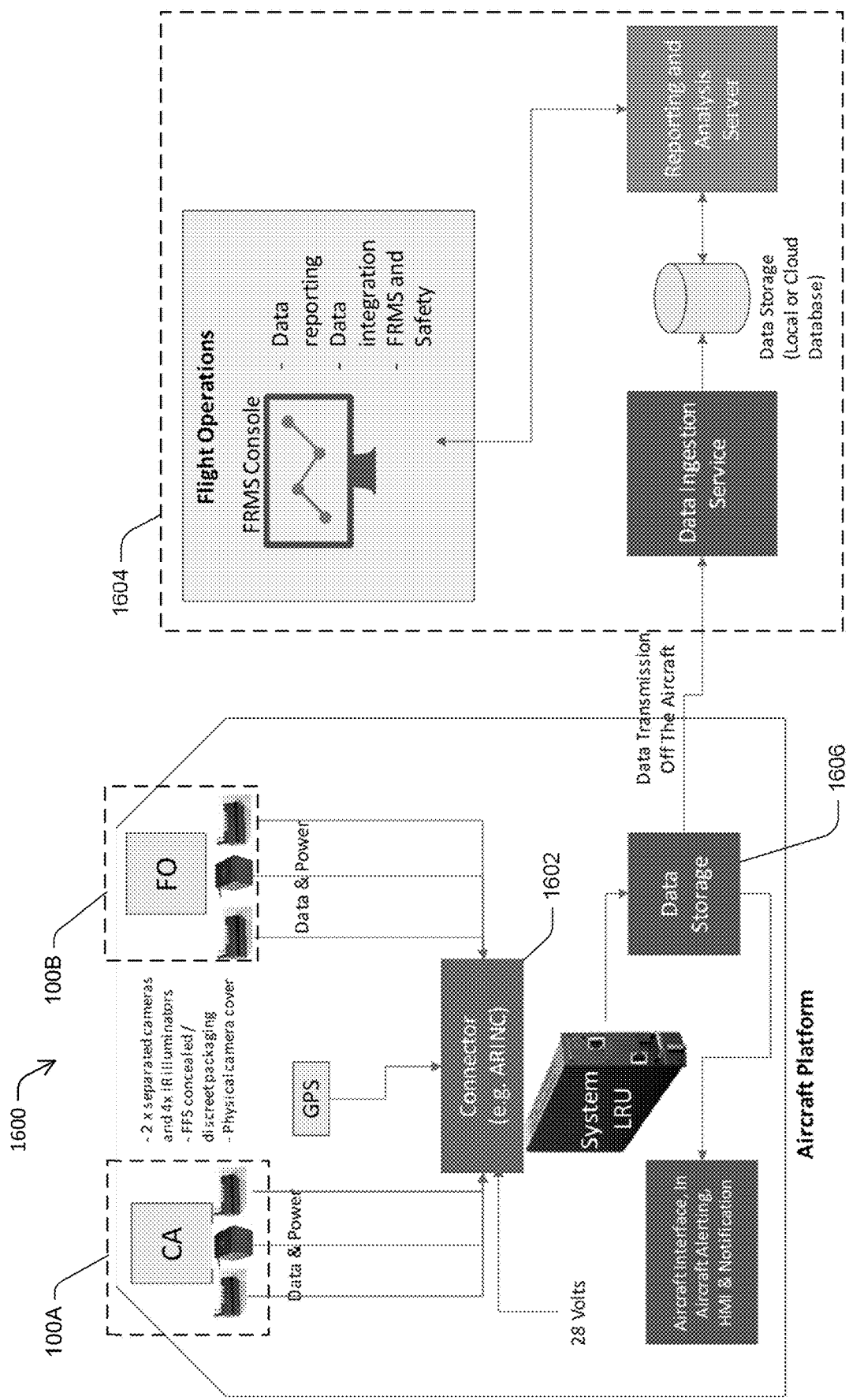
FIG. 16 is a schematic system diagram illustrating an example aircraft data system having two pilot monitoring systems integrated therein.

Referring now to FIG. 15, there is illustrated a method 1500 of monitoring a pilot/co-pilot during a period of controlled rest. Method 1500 is performed by system 100 as described above. Method 1500 includes the initial step 1501 of detecting a controlled rest event for the pilot 102 or co-pilot 103 based on visual detection of a sleep state by system 100 and optionally also a current phase of flight. Alternatively, the controlled rest event may be detected by system 100 via a manual designation by the pilot/co-pilot prior to resting or by the non-resting pilot/co-pilot via input on instrument panel 107. The controlled rest event may be triggered directly by system 100 as an output of method 1300.

At step 1502, system 100 optionally monitors the duration of controlled rest event by detecting when the resting pilot/co-pilot enters and remains in a sleep state with their eyes closed. System 100 may be pre-programmed to ensure the resting pilot/co-pilot does not rest longer than a predetermined period such as 30-45 minutes to ensure there is suitable time for recovery from sleep inertia. Step 1502 is illustrated as a dashed box as it is optional. Method 1500 may be performed without step 1502 as the duration may be monitored manually or by another part of the flight management system of aircraft 104. Step 1502 is only possible where the resting pilot/co-pilot takes an in-seat rest and does not leave the cockpit.

At step 1502, system 100 may also be capable of detecting a sleep state of the pilot 102 or co-pilot 103 who is sleeping during a period of controlled rest. By way of example, these sleep states may be characterized at least in part by the 5 stages of sleep defined by the American Sleep Association. This sleep detection may be achieved by detecting the head movement, body movement and eyelid movement of the pilot/co-pilot in the captured images during sleep. Detection of a high degree of head or body movement may suggest a lower quality sleep or lighter sleep state (Stage 1 and 2 NREM Sleep). Conversely, detection of rapid eye movement may suggest the resting pilot/co-pilot is in a REM sleep state. And the detection of an absence of body movement may suggest a deeper state of Stage 3 NREM Sleep, or Slow Wave Sleep (SWS), typically referred to as Stage 4 Deep Sleep. System 100 may be able to estimate a during in which the resting pilot/co-pilot has been in a specific sleep state and optionally wake the pilot/co-pilot if they are likely to enter a deep sleep state. By way of example, system 100 may detect that the resting pilot/co-pilot has been in NREM sleep state for 20 minutes based on detection of their body and eyelid movement. In this case, there is a risk that the resting pilot/co-pilot will enter a deep sleep state so an alert may be issued to wake the pilot/co-pilot.

As mentioned above, in some embodiments, system 100 includes additional hardware adapted to monitor biometric information of the pilot 102 and/or co-pilot 103. In step 1502, biometric information may be received from the pilot 102 and/or co-pilot 103 from a biometric reader device to determine a sleep state of the resting pilot/co-pilot. By way of example, the pilot/co-pilot's brain activity may be monitored from an attached EEG device connected to the pilot/co-pilot to determine if a deep sleep state has been reached.

At step 1503, system 100 monitors the alertness state of the pilot or co-pilot who is awake during a detected controlled rest period. This monitoring may include the same or similar techniques described above in relation to step 1302 by processing the images captured by camera 106 to monitor the alertness of the non-resting pilot/co-pilot.

Steps 1502 and 1503 occur in conjunction with each other and are interchangeable in order. That is, steps 1502 and 1503 represent ongoing monitoring by system 100 throughout the detected controlled rest event.

At step 1504, system 100 issues an alert if the non-resting pilot/co-pilot enters a predetermined alertness state such as a distracted state, low vigilance drowsy state, asleep state or incapacitated attention state. The alert is preferably issued via the instrument panel 107 or other device in the cockpit and may be visual, audio, tactile, haptic or audiovisual in nature. The alert may also be issued to cabin crew outside the cockpit via a signal transmitted to a cabin crew notification system/device. This allows a cabin crew member to visit the cockpit to check on the non-resting pilot/co-pilot. An alert may also be issued if system 100 detects that the resting pilot/co-pilot has been asleep for a predetermined period of rest and/or the aircraft requires attention by both the pilot and co-pilot.

In some embodiments, method 1500 includes the step of issuing an alert to the non-resting pilot/co-pilot if a deep sleep state of the resting pilot/co-pilot is detected by system 100. The alert may be issued to the non-resting pilot/co-pilot or may be issued to the resting pilot/co-pilot to wake the resting pilot/co-pilot. The determination of whether or not to issue this alert may be based on the calculation that the resting pilot/co-pilot will require a sleep inertia recovery period that is longer than a predetermined time period.

Where appropriate permission is obtained, system 100 may also be capable of performing facial recognition on at least a subset of the digital images captured by camera 106 to detect an identity of the pilot and/or co-pilot. This facial recognition may be performed initially to ensure the pilot 102 and co-pilot 103 are the authorized personnel and may be used to access that person's past sleep or duty history, or other relevant personal data. Strict privacy protocols must be implemented into system 100 to ensure pilot's personal and biometric data is stored safely. Facial recognition may also be performed throughout the flight to identify who is the pilot 102 and who is the co-pilot 103 should they swap seats, move around the cockpit or exit/enter the cockpit from the cabin. This allows system 100 to accurately track the correct subject and apply any known sleep or duty history to the correct person for determining an attention state.

System 100 may also be capable of performing object detection on at least a subset of the digital images to determine the presence of other people or objects in the cockpit of the aircraft 104. When other people such as known cabin crew members enter the cockpit, facial recognition may also be used to identify these third parties entering the cockpit and detect a person in the cockpit who is not the pilot or co-pilot or who may be unauthorized to be in the cockpit. The object detection may also be capable of detecting the presence of a weapon or other dangerous object in the cockpit.

Where it is required or advantageous to do so, system 100 may be capable of registering the timing of known cabin crew members visiting the cockpit to check on the pilot/co-pilot. This may be during a period of controlled rest of the pilot/co-pilot or during normal flight conditions. Such check-ins by cabin crew may be a requirement or a preferred operating procedure to ensure that the non-resting pilot/co-pilot has not fallen asleep or become too drowsy. System 100 may also be capable of alerting one or more cabin crew members if a non-resting pilot/co-pilot is detected as becoming drowsy during a controlled rest period.

Referring now to FIG. 116, there is illustrated schematically an example aircraft data system 1600 showing how pilot monitoring system 160 can be integrated into the aircraft. As illustrated, System 100A monitoring a captain (CA) and system 100B monitoring a first officer (FO) can be integrated into the aircraft data system via an electrical data connector such as an ARINC 429 connector 1602, which is standard in most aircraft. This allows data to be transmitted to devices stored in an electronics bay of the aircraft and communicated to external data systems 1604 such as ground control for monitoring. The data may also be stored on a data storage device 1606 of the aircraft for subsequent analysis, reporting and safety improvement purposes. Many of the elements of system 1600 can be integrated into the aircraft's interfacing device as described above.

The above described system allows for accurately monitoring an attention state of pilots/co-pilots of aircraft and determining suitable controlled rest events for pilots/co-pilots during flight. This can facilitate the safe resting of fatigued pilots/co-pilots, leading to more alert pilots/co-pilots during critical phases of flight such as landing.

The data obtained from system 100, including pilot/co-pilot alertness levels and controlled rest periods can be stored and subsequently analyzed by the pilot/co-pilot or other parties. This analysis can be useful in pilots and other parties reviewing pilot performance, alertness and sleep effects post flight. In particular, this data can yield useful information such as the positive and negative effects of controlled rest periods on subsequent alertness of pilots. By way of example, this post-flight data may be made available via a software application such as a mobile device app or Electronic Flight Bag ("EFB").

A CFRMS as described above assists the flight and cabin crew members to be sufficiently alert so they can operate to a satisfactory level of performance. It applies principles and processes from Safety Management Systems (SMS) to manage the specific risks associated with crewmember fatigue. Like SMS, CFRMS seeks to achieve a realistic balance between safety, productivity, and costs. It seeks to proactively identify opportunities to improve operational processes and reduce risk, as well as identifying deficiencies after adverse events. The structure of a CFRMS as described here is modelled on the SMS framework. The core activities are safety risk management (described in the SARPS as FRM processes) and safety assurance (described in the SARPs as CFRMS safety assurance processes). These core activities are governed by an CFRMS policy and supported by CFRMS promotion processes, and the system must be documented.

Interpretation

The term "infrared" is used throughout the description and specification. Within the scope of this specification, infrared refers to the general infrared area of the electromagnetic spectrum which includes near infrared, infrared and far infrared frequencies or light waves.

Unless specifically stated otherwise, as apparent from the following discussions, it is appreciated that throughout the specification discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "controller" or "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

Reference throughout this specification to "one embodiment", "some embodiments" or "an embodiment" means that a particular feature, structure or characteristic described in connection with the embodiment is included in at least one embodiment of the present disclosure. Thus, appearances of the phrases "in one embodiment", "in some embodiments" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

It should be appreciated that in the above description of exemplary embodiments of the disclosure, various features of the disclosure are sometimes grouped together in a single embodiment, Fig., or description thereof for the purpose of streamlining the disclosure and aiding in the understanding of one or more of the various inventive aspects. This method of disclosure, however, is not to be interpreted as reflecting an intention that the claims require more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical, electrical or optical contact, or that two or more elements are not in direct contact with each other but yet still co-operate or interact with each other.

Embodiments described herein are intended to cover any adaptations or variations of the present invention. Although the present invention has been described and explained in terms of particular exemplary embodiments, one skilled in the art will realize that additional embodiments can be readily envisioned that are within the scope of the present invention.

What is claimed is:

1. A pilot monitoring method, including:
   receiving, from one or more cameras, a plurality of digital images of an aircraft cockpit including both a pilot and a co-pilot in the infrared wavelength range;
   controlling an image processor to process the received images to simultaneously determine an alertness state of both the pilot and the co-pilot during operation of the aircraft based on detected facial and/or body features of the pilot and co-pilot in the images;
   displaying the alertness state to the pilot and co-pilot in real-time;
   transmitting the alertness state of the pilot and co-pilot to a remote database that is accessible to ground crew; and
   generating a post-flight fatigue report including objective fatigue level throughout the flight for the pilot and the co-pilot;
   receiving information indicative of a current or future phase of flight of the aircraft;
   determining, based on the alertness state of the pilot and the co-pilot and the current phase of flight, an amount and/or type of a controlled rest period for the pilot or co-pilot;
   wherein the post-flight fatigue report indicates whether the controlled rest event was used successfully.

2. The method according to claim 1 wherein the processor is further configured to receive input indicative of sleep history and/or a recent duty history of the pilot and/or co-pilot and wherein the determination of a controlled rest period for the pilot or co-pilot is based on the sleep/duty history.

3. The method according to claim 1 including the step of receiving input from the pilot or co-pilot to specify a controlled rest event.

4. The method according to claim 1 including the step of performing facial recognition on at least a subset of the digital images to detect a presence of known cabin crew members in the cockpit.

5. The method according to claim 1 including receiving biometric information of the pilot and/or co-pilot from a biometric reader device and wherein the determination of a controlled rest period for either the pilot or co-pilot is based on the received biometric information.

6. The method according to claim 1 wherein the alertness state is calculated based at least in part on a detected body position of the pilot and/or co-pilot in the received images.

7. The method according to claim 1 wherein the alertness state is calculated based at least in part on detected head and/or body motion of the pilot and/or co-pilot across a plurality of the received images.

8. The method according to claim 1 wherein the alertness state is calculated based at least in part on detected mouth movement of the pilot and/or co-pilot across a plurality of the received images.

9. The method according to claim 1 wherein the alertness state is calculated based at least in part on detected speech of the pilot and/or co-pilot.

10. The method according to claim 1 wherein the alertness state is characterized at least in part by a drowsiness measure based on the Karolinska Sleepiness Scale or Samn-Perelli scale.

11. The method according to claim 1 including the step of issuing a wake up alert to a resting pilot once a period of controlled rest ends.

12. The method according to claim 1 wherein the step of displaying the alertness state to the pilot and co-pilot includes visualising the alertness state on a graphical user interface in the cockpit.

13. The method according to claim 1 including the step of issuing a pilot briefing to the pilot or co-pilot based on a current or past alertness state.

14. The method according to claim 13 wherein the pilot briefing is issued during the flight.

15. The method according to claim 13 wherein the pilot briefing is issued post-flight.

16. The method according to claim 15 wherein the post-flight briefing includes a current or future predicted fatigue or alertness level of pilot or co-pilot.

17. The method according to claim 15 wherein the post-flight briefing includes a future flight or rest schedule for the pilot or co-pilot.

18. The method according to claim 1 including the step of issuing a first alert to the pilot and/or co-pilot including a determination of a controlled rest period for either the pilot or co-pilot.

19. The method according to claim 18 including the step of detecting a controlled rest event for the pilot or co-pilot based on detection of a sleep state or an elevated drowsiness state and a current phase of flight.

20. The method according to claim 19 including the step of monitoring the visual alertness state of the pilot or co-pilot who is awake during a detected controlled rest period of either the pilot or co-pilot.

21. The method according to claim 20 including the step of issuing a second alert if the pilot or co-pilot who is awake enters a distracted, low vigilance drowsy, asleep or incapacitated attention state.

22. The method according to claim 21 wherein the second alert includes an alert that a pilot is drowsy and which is issued to an in-aircraft crew rest facility within the aircraft.

23. The method according to claim 21 wherein the second alert includes a notification that a controlled rest period has been entered and which is issued to a cabin crew notification device to alert a cabin crew member.

24. The method according to claim 21 wherein the second alert is issued to a ground terminal to alert a dispatch, safety or operations member of a controlled rest period.

25. The method according to claim 1 wherein the post-flight briefing provides risk analysis and pilot pairing analysis.

26. The method according to claim 1 wherein the post-flight briefing is based at least in part on historical objective pilot fatigue data.

27. A pilot monitoring system, including:
one or more cameras configured to capture a plurality of digital images of an aircraft cockpit including both a pilot and a co-pilot; and
a processor configured to process the captured images to:
determine an alertness state of both the pilot and the co-pilot during operation of the aircraft based on detected facial and/or body features of the pilot and/or co-pilot in the images;
a display configured to display the alertness state to the pilot and co-pilot in real-time;
a communications module configured to transmit the alertness state of the pilot and co-pilot to a remote database that is accessible to ground crew; and
a remote database configured to generate a post-flight fatigue report of the pilot and co-pilot that is available to ground crew;
receive information indicative of a current or future phase of flight of the aircraft;
determine, based on the alertness state of the pilot and the co-pilot and the current phase of flight, an amount and/or type of a controlled rest period for the pilot or co-pilot;
wherein the post-flight fatigue report indicates whether the controlled rest event was used successfully.

28. The system according to claim 27 including a single wide angle camera positioned to simultaneously image the pilot and co-pilot.

* * * * *